US012667500B2

(12) United States Patent
Liedl

(10) Patent No.: US 12,667,500 B2
(45) Date of Patent: Jun. 30, 2026

(54) ARTICLES WITH ZONED APERTURED MATERIALS AND REGISTRATION METHODS

(71) Applicant: Kimberly-Clark Worldwide, Inc., Neenah, WI (US)

(72) Inventor: Max S. Liedl, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 509 days.

(21) Appl. No.: 18/251,983

(22) PCT Filed: Dec. 30, 2020

(86) PCT No.: PCT/US2020/067485
§ 371 (c)(1),
(2) Date: May 5, 2023

(87) PCT Pub. No.: WO2022/146428
PCT Pub. Date: Jul. 7, 2022

(65) Prior Publication Data
US 2024/0009039 A1     Jan. 11, 2024

(51) Int. Cl.
*A61F 13/15* (2006.01)
*A61F 13/512* (2006.01)
(52) U.S. Cl.
CPC ...... *A61F 13/15772* (2013.01); *A61F 13/512* (2013.01); *A61F 2013/1578* (2013.01); *A61F 2013/15796* (2013.01)
(58) Field of Classification Search
CPC .............. A61F 13/15772; A61F 13/512; A61F 2013/1578; A61F 2013/15796
See application file for complete search history.

(56) References Cited

U.S. PATENT DOCUMENTS 5,969,373 A     10/1999 Harris
6,404,910 B1     6/2002 Ungpiyakul et al.
(Continued)

FOREIGN PATENT DOCUMENTS

CN     110559077 A     12/2019
WO     2000037249 A1     6/2000
WO     2005043141 A1     5/2005

OTHER PUBLICATIONS

Mohan, Arun et al., "Crack detection using image processing: A critical review and analysis", Science Direct, Feb. 15, 2017, https://www.sciencedirect.com/science/article/pii/S1110016817300236.
(Continued)

*Primary Examiner* — George R Koch
*Assistant Examiner* — Christopher C Caillouet
(74) *Attorney, Agent, or Firm* — KIMBERLY-CLARK WORLDWIDE, INC.

(57) ABSTRACT

Absorbent articles comprising apertured regions and methods of manufacture and registration are disclosed. In an embodiment, a method of registering webs comprises moving first and second webs in a machine direction, capturing a first image comprising a portion of the second web, filtering the captured first image to determine one or more regions of the captured first image having a light transmittance value greater than the transmittance threshold value, modifying the captured first image with a dilation morphological operation, determining a feature of interest, determining a first difference value comprising a difference in location between the feature of interest and a reference feature of the captured first image or the modified captured first image, adjusting a speed of the second web in the machine direction, and coupling the first web and the second web together.

19 Claims, 8 Drawing Sheets

(56)                    References Cited

U.S. PATENT DOCUMENTS

| | | | |
|---|---|---|---|
| 6,624,885 B1 | 9/2003 | Pon et al. | |
| 7,623,699 B2 | 11/2009 | Floeder et al. | |
| 7,797,133 B2 | 9/2010 | Floeder et al. | |
| 8,023,720 B2 | 9/2011 | Reunanen et al. | |
| 8,270,701 B2 | 9/2012 | Floeder et al. | |
| 10,002,438 B2 | 6/2018 | Pollard et al. | |
| 2004/0019400 A1* | 1/2004 | Popp et al. | |
| 2010/0305738 A1* | 12/2010 | DeBruler | A61F 13/15772 |
| | | | 709/248 |
| 2011/0243425 A1* | 10/2011 | Maltbie | A61F 13/15203 |
| | | | 382/154 |
| 2014/0037299 A1 | 2/2014 | Nakura et al. | |
| 2017/0258650 A1* | 9/2017 | Rosati | D04H 1/42 |
| 2018/0214321 A1 | 8/2018 | Ashraf et al. | |
| 2018/0227564 A1 | 8/2018 | Wolf et al. | |
| 2019/0240082 A1 | 8/2019 | Mullane et al. | |

OTHER PUBLICATIONS

Datta, Asit et al., "Detection of Defects in Fabric by Morphological Image Processing", Research Gate, Aug. 2010, https://www.researchgate.net/publication/221905536_Detection_of_Defects_in_Fabric_by_Morphological_Image_Processing/link/0fcfd50f6719ddf4f6000000/download.
Ragupathy, U.S. et al., "Fault Identification and Classification in Textile Web Materials using Particle Analyzer", International Conference on Intelligent Computational Systems, Apr. 29-30, 2013, http://psrcentre.org/images/extraimages/14%20413657.pdf.

* cited by examiner

*200*

CAPTURE FIRST IMAGE OF APERTURED MATERIAL WITH FIRST CAPTURE DEVICE — *202*

DETERMINE APERTURED AREA, APERTURED AREA FEATURE OF INTEREST, AND REFERENCE FEATURE IN FIRST IMAGE — *204*

DETERMINE DIFFERENCE IN LOCATION OF APERTURED AREA FEATURE OF INTEREST AND REFERENCE FEATURE IN FIRST IMAGE — *206*

ADJUST INFEED SPEED OF APERTURED MATERIAL BASED ON DETERMINED DIFFERENCE — *208*

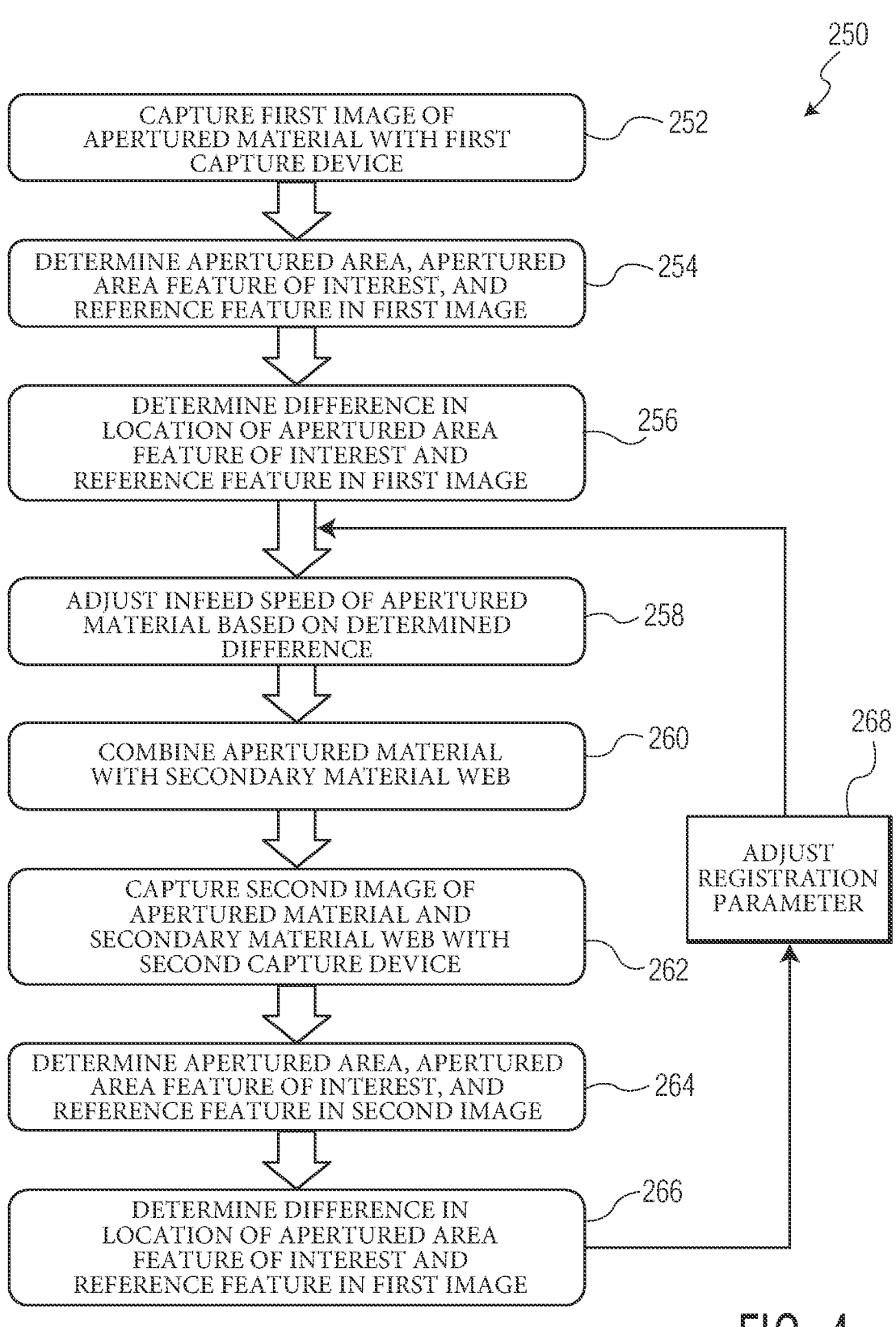

250

CAPTURE FIRST IMAGE OF
APERTURED MATERIAL WITH FIRST
CAPTURE DEVICE — 252

DETERMINE APERTURED AREA, APERTURED
AREA FEATURE OF INTEREST, AND
REFERENCE FEATURE IN FIRST IMAGE — 254

DETERMINE DIFFERENCE IN
LOCATION OF APERTURED AREA
FEATURE OF INTEREST AND
REFERENCE FEATURE IN FIRST IMAGE — 256

ADJUST INFEED SPEED OF APERTURED
MATERIAL BASED ON DETERMINED
DIFFERENCE — 258

COMBINE APERTURED MATERIAL
WITH SECONDARY MATERIAL WEB — 260

268

ADJUST
REGISTRATION
PARAMETER

CAPTURE SECOND IMAGE OF
APERTURED MATERIAL AND
SECONDARY MATERIAL WEB WITH
SECOND CAPTURE DEVICE — 262

DETERMINE APERTURED AREA, APERTURED
AREA FEATURE OF INTEREST, AND
REFERENCE FEATURE IN SECOND IMAGE — 264

DETERMINE DIFFERENCE IN
LOCATION OF APERTURED AREA
FEATURE OF INTEREST AND
REFERENCE FEATURE IN FIRST IMAGE — 266

FIG. 4

ARTICLES WITH ZONED APERTURED MATERIALS AND REGISTRATION METHODS

TECHNICAL FIELD

The present disclosure relates to apertured materials. More particularly, the present disclosure relates to zoned apertured materials for use in absorbent articles and methods of registering the zoned apertures.

BACKGROUND OF THE DISCLOSURE

A primary function of personal care absorbent articles is to absorb and retain body exudates such as urine, fecal material, blood, and menses with additional desired attributes including low leakage of the exudates from the absorbent article and a dry feel to the wearer of the absorbent article. By preventing leakage of the exudates from the absorbent article, the absorbent article intends to prevent the body exudates from soiling or contaminating a wearer's or caregiver's clothing or other articles, such as bedding, that can come in contact with the wearer.

One effective manner to help body exudates quickly absorb into such articles for long-term storage and retention, such as within an absorbent body or the like, is to provide apertures in a topsheet material of the article. Thus, such apertured topsheet materials may help to draw body exudates away from a wearer's skin and isolate the wearer's skin from the body exudates—which helps maintain comfort and skin health of a wearer. However, it may be less advantageous to provide apertures all throughout the topsheet. For example, such apertures may be particularly advantageous for drawing semi-solid fecal material, such as low viscosity fecal material, which can be prevalent with younger children, into an interior of an article. However, such apertures may be less advantageous for handling urine exudates, as such apertures may provide an avenue for urine exudates to transfer back to a wearer's skin, typically termed rewetting.

Accordingly, there is a need for articles having zoned apertured regions to capture the benefits of such apertures while minimizing drawbacks. Additionally, processes and apparatuses for positioning such zoned apertured regions consistently and accurately within absorbent article products are needed.

SUMMARY OF THE DISCLOSURE

In one embodiment, a method of registering first and second simultaneously advancing webs may comprise moving a continuous first web in a machine direction, moving a continuous second web in the machine direction in proximity to the first web, the second web comprising one or more first portions having a light transmittance value below a transmittance threshold value and one or more second portions having a light transmittance value greater than or equal to the transmittance threshold value, capturing, with a registration system comprising an image capture device coupled to a registration processing device, a first image comprising a portion of the second web, filtering, with the registration processing device, the captured first image to determine one or more regions of the captured first image having a light transmittance value greater than the transmittance threshold value, modifying, with the registration processing device, the captured first image by applying a dilation morphological operation to the filtered captured first image, determining, with the registration processing device and based at least in part on the modified captured first image, a feature of interest related to the determined one or more regions, determining, with the registration processing device, a first difference value comprising a difference in location between the feature of interest and a reference feature of the captured first image or the modified captured first image, adjusting, based at least in part on the determined first difference value, a speed of the second web in the machine direction, and coupling the first web and the second web together.

In another embodiment, a method of registering a first web and an apertured region of a second web may comprise moving a continuous first web in a machine direction, moving a continuous second web in the machine direction in proximity to the first web, the second web comprising a plurality of apertures forming a plurality of discrete apertured regions spaced apart from each other in the machine direction, capturing, with a registration system comprising an image capture device coupled to a registration processing device, a first image comprising a portion of the second web, filtering, with the registration processing device, the captured first image to determine one or more apertured regions of the captured first image, modifying, with the registration processing device, the filtered captured first image by applying a dilation morphological operation to the filtered captured first image, determining, with the registration processing device and based at least in part on the modified filtered captured first image, a feature of interest related to the determined one or more apertured regions, determining, with the registration processing device, a first difference value comprising a difference in location between the feature of interest and a reference feature of the captured first image or the modified filtered captured first image, adjusting, based at least in part on the determined first difference value, a relative position of a discrete apertured region of first web with respect to the second web, and combining the first web and the second web.

In yet another embodiment, a method of registering a first web and an apertured region of a second web may comprise moving a continuous first web in a machine direction, moving a continuous second web in the machine direction in proximity to the first web, the second web comprising a plurality of apertures forming a plurality of discrete apertured regions spaced apart from each other in the machine direction, capturing, with a registration system comprising a first image capture device coupled to a registration processing device, a first image comprising a portion of the second web, determining, with the registration processing device, a first difference value comprising a difference in location between a first feature of interest and a first reference feature of the captured first image, adjusting, based at least in part on registration parameters including the determined first difference value and a first difference value threshold, a relative position of a discrete apertured region of the second web with respect to the first web, combining the first web and the second web, capturing, with the registration system by a second image capture device coupled to the registration processing device, a second image comprising a portion of the combined first web and second web, determining, with the registration processing device, a second difference value comprising a difference in location between a second feature of interest and a second reference feature of the captured second image, and adjusting, with the registration processing device and based at least on the determined second difference value, at least one of the registration parameters.

BRIEF DESCRIPTION OF DRAWINGS

A full and enabling disclosure thereof, directed to one of ordinary skill in the art, is set forth more particularly in the remainder of the specification, which makes reference to the appended figures in which:

FIG. 4 is a process flow diagram of a further exemplary registration method according to aspects of the present disclosure.

Figure 1:
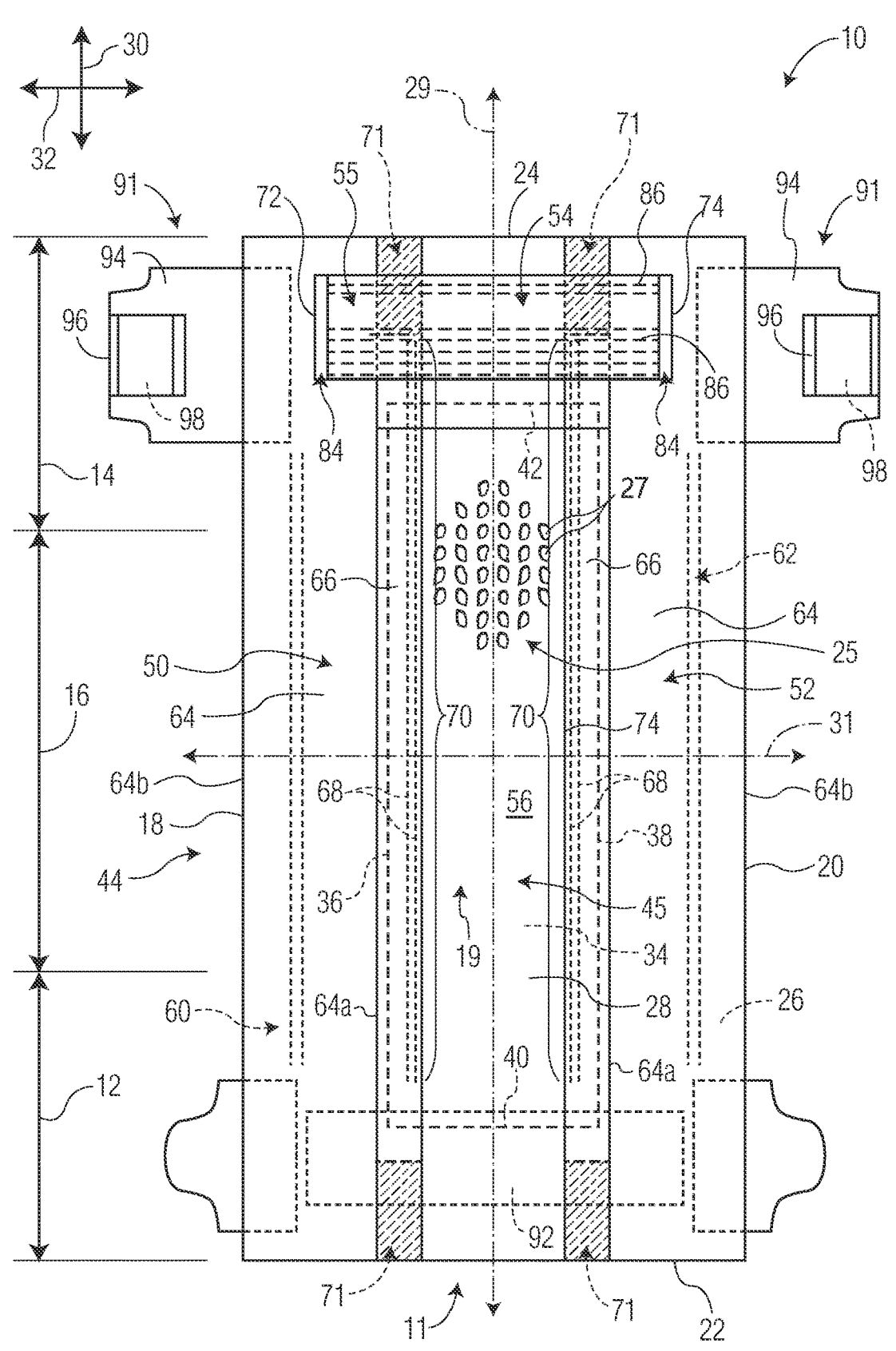
FIG. 1 is a top plan view of an exemplary absorbent article according to aspects of the present disclosure and in a stretched, laid flat, unfastened condition.

Repeat use of reference characters in the present specification and drawings is intended to represent the same or analogous features or elements of the disclosure.

DETAILED DESCRIPTION OF THE DISCLOSURE

In an embodiment, the present disclosure is generally directed towards an absorbent article having a zoned apertured topsheet material. Each example is provided by way of explanation and is not meant as a limitation. For example, features illustrated or described as part of one embodiment or figure can be used on another embodiment or figure to yield yet another embodiment. It is intended that the present disclosure include such modifications and variations.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

Definitions

The term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, diaper pants, training pants, youth pants, swim pants, feminine hygiene products, including, but not limited to, menstrual pads or pants, incontinence products, medical garments, surgical pads and bandages, other personal care or health care garments, and the like without departing from the scope of the present disclosure.

The term "acquisition layer" refers herein to a layer capable of accepting and temporarily holding liquid body exudates to decelerate and diffuse a surge or gush of the liquid body exudates and to subsequently release the liquid body exudates therefrom into another layer or layers of the absorbent article.

The term "bonded" or "coupled" refers herein to the joining, adhering, connecting, attaching, or the like, of two elements. Two elements will be considered bonded or coupled together when they are joined, adhered, connected, attached, or the like, directly to one another or indirectly to one another, such as when each is directly bonded to intermediate elements. The bonding or coupling of one element to another can occur via continuous or intermittent bonds.

The term "carded web" refers herein to a web containing natural or synthetic staple length fibers typically having fiber lengths less than about 100 mm. Bales of staple fibers can undergo an opening process to separate the fibers which are then sent to a carding process which separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers may be subject to adhesive processes to bind the fibers together such as by the use of powder adhesives. The carded web may be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "dilation morphological operation" refers herein to an image processing technique wherein an image is modified resulting in a dilated image.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer fluids, such as, but not limited to, barrier films, filled films, breathable films, and oriented films.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers which may be continuous or discontinuous, are generally smaller than about 0.6 denier, and may be tacky and self-bonding when deposited onto a collecting surface.

The term "nonwoven" refers herein to materials and webs of material which are formed without the aid of a textile weaving or knitting process. The materials and webs of materials can have a structure of individual fibers, filaments, or threads (collectively referred to as "fibers") which can be interlaid, but not in an identifiable manner as in a knitted fabric. Nonwoven materials or webs can be formed from many processes such as, but not limited to, meltblowing processes, spunbonding processes, carded web processes, etc.

The term "pliable" refers herein to materials which are compliant and which will readily conform to the general shape and contours of the wearer's body.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as, for example, educative drawing, and processes that are described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6, 5 and 10 and about 15, 20 and 40. Spunbond fibers are generally not tacky when they are deposited on a collecting surface.

The term "superabsorbent" refers herein to a water-swellable, water-insoluble organic or inorganic material capable, under the most favorable conditions, of absorbing at least about 15 times its weight and, in an embodiment, at least about 30 times its weight, in an aqueous solution containing weight percent sodium chloride. The superabsorbent materials can be natural, synthetic and modified natural polymers and materials. In addition, the superabsorbent materials can be inorganic materials, such as silica gels, or organic compounds, such as cross-linked polymers.

The term "thermoplastic" refers herein to a material which softens and which can be shaped when exposed to heat and which substantially returns to a non-softened condition when cooled.

The term "user" or "caregiver" refers herein to one who fits an absorbent article, such as, but not limited to, a diaper, diaper pant, training pant, youth pant, incontinent product, or other absorbent article about the wearer of one of these absorbent articles. A user and a wearer can be one and the same person.

Absorbent Article:

Referring to FIG. 1, a non-limiting illustration of an exemplary absorbent article 10 according to aspects of the present disclosure, for example a diaper, is illustrated. Other embodiments of the absorbent article could include training pants, youth pants, adult incontinence garments, and feminine hygiene articles, and the like. While the embodiments and illustrations described herein may generally apply to absorbent articles manufactured in the product longitudinal direction, which is hereinafter called the machine direction or process direction manufacturing of a product, it should be noted that one of ordinary skill in the art could apply the information herein to absorbent articles manufactured in the latitudinal direction of the product, which hereinafter is called the cross direction manufacturing of a product, without departing from the spirit and scope of the disclosure.

The absorbent article 10 illustrated in FIG. 1 can include a chassis 11. The absorbent article further can include a front waist region 12, a rear waist region 14, and a crotch region 16 disposed between the front waist region 12 and the rear waist region 14 and interconnecting the front and rear waist regions, 12, 14, respectively. The front waist region 12 can be referred to as the front end region, the rear waist region 14 can be referred to as the rear end region, and the crotch region 16 can be referred to as the intermediate region. With respect to an article manufactured in a cross-direction manufacturing process, for example in a three-piece construction, such an absorbent article can have a chassis including a front waist panel defining the front waist region, a rear waist panel defining the rear waist region, and an absorbent panel defining the crotch region. The absorbent panel can extend between the front waist panel and the rear waist panel. In some embodiments, the absorbent panel can overlap the front waist panel and the rear waist panel. The absorbent panel can be bonded to the front waist panel and the rear waist panel to define a three-piece construction. However, it is contemplated that an absorbent article can be manufactured in a cross-direction without being a three-piece construction garment.

The absorbent article 10 can have a pair of longitudinal side edges 18, 20, and a pair of opposite waist edges, respectively designated front waist edge 22 and rear waist edge 24. The front waist region 12 can be contiguous with the front waist edge 22 and the rear waist region 14 can be contiguous with the rear waist edge 24. The longitudinal side edges 18, 20 can extend from the front waist edge 22 to the rear waist edge 24. The longitudinal side edges 18, 20 can extend in a direction parallel to the longitudinal direction 30 for their entire length, such as for the absorbent article 10. In other embodiments, the longitudinal side edges 18, 20 can be curved between the front waist edge 22 and the rear waist edge 24.

The front waist region 12 can include the portion of the absorbent article 10 that, when worn, is positioned at least in part on the front of the wearer while the rear waist region 14 can include the portion of the absorbent article 10 that, when worn, is positioned at least in part on the back of the wearer.

The crotch region 16 of the absorbent article 10 can include the portion of the absorbent article 10 that, when worn, is positioned between the legs of the wearer and can partially cover the lower torso of the wearer. The waist edges, 22 and 24, of the absorbent article 10 are configured to encircle the waist of the wearer and together define a central waist opening for the waist of the wearer. Portions of the longitudinal side edges 18, 20 in the crotch region 16 can generally define leg openings for the legs of the wearer when the absorbent article 10 is worn.

The absorbent article 10 can include an outer cover 26 and a bodyside liner 28. The outer cover 26 and the bodyside liner 28 can form a portion of the chassis 11. In an embodiment, the bodyside liner 28 can be bonded to the outer cover 26 in a superposed relation by any suitable means such as, but not limited to, adhesives, ultrasonic bonds, thermal bonds, pressure bonds, or other conventional techniques. The outer cover 26 can define a length in a longitudinal direction 30, and a width in the lateral direction 32, which, in the illustrated embodiment, can coincide with the length and width of the absorbent article 10. As illustrated in FIG. 1, the absorbent article 10 can have a longitudinal axis 29 extending in the longitudinal direction 30 and a lateral axis 31 extending in the lateral direction 32.

The chassis 11 can include an absorbent body 34. The absorbent body 34 can be disposed between the outer cover 26 and the bodyside liner 28. The absorbent body 34 can have longitudinal edges, 36 and 38, which, in an embodiment, can form portions of the longitudinal side edges, 18 and 20, respectively, of the absorbent article 10. The absorbent body 34 can have a first end edge 40 that is opposite a second end edge 42, respectively, which, in an embodiment, can form portions of the waist edges, 22 and 24, respectively, of the absorbent article 10. In some embodiments, the first end edge 40 can be in the front waist region 12. In some embodiments, the second end edge 42 can be in the rear waist region 14. In an embodiment, the absorbent body 34 can have a length and width that are the same as or less than the length and width of the absorbent article 10. The bodyside liner 28, the outer cover 26, and the absorbent body 34 can form part of an absorbent assembly 44. In embodiments of articles according to aspects of the present disclosure which are manufactured in a cross-direction manufacturing process, the absorbent panel can form the absorbent assembly 44. The absorbent assembly 44 can also include a fluid transfer layer (not shown) and/or a fluid acquisition layer (not shown) between the bodyside liner 28 and the absorbent body 34 as is known in the art. The absorbent assembly 44 can also include a spacer layer (not shown) disposed between the absorbent body 34 and the outer cover 26.

The absorbent article 10 can be configured to contain and/or absorb liquid, solid, and semi-solid body exudates discharged from the wearer. In some embodiments, containment flaps 50, 52 can be configured to provide a barrier to the lateral flow of body exudates. To further enhance containment and/or absorption of body exudates, the absorbent article 10 can suitably include an elasticated waist member 54. In some embodiments, the elasticated waist member 54 can be disposed in the rear waist region 14 of the absorbent article 10. Although, it is contemplated that the elasticated waist member 54 can be additionally or alternatively disposed in the front waist region 12 of the absorbent article 10.

The elasticated waist member 54 can be disposed on the body facing surface 19 of the chassis 11 to help contain and/or absorb body exudates. In some embodiments, such as in the absorbent article 10 depicted in FIG. 1, the elasticated waist member 54 can be disposed on the body facing surface 45 of the absorbent assembly 44. In some embodiments, the elasticated waist member 54 can be disposed at least partially on the body facing surface 56 of the bodyside liner 28.

The absorbent article 10 can further include leg elastic members 60, 62 as are known to those skilled in the art. The leg elastic members 60, 62 can be attached to the outer cover 26 and/or the bodyside liner 28 along the opposite longitudinal side edges, 18 and 20, and positioned in the crotch region 16 of the absorbent article 10. The leg elastic members 60, 62 can be parallel to the longitudinal axis 29 as shown in FIG. 1, or can be curved as is known in the art. The leg elastic members 60, 62 can provide elasticized leg cuffs.

Outer Cover:

The outer cover 26 and/or portions thereof can be breathable and/or liquid impermeable. The outer cover 26 and/or portions thereof can be elastic, stretchable, or non-stretchable. The outer cover 26 may be constructed of a single layer, multiple layers, laminates, spunbond fabrics, films, meltblown fabrics, elastic netting, microporous webs, bonded-carded webs or foams provided by elastomeric or polymeric materials. In an embodiment, for example, the outer cover 26 can be constructed of a microporous polymeric film, such as polyethylene or polypropylene.

In an embodiment, the outer cover 26 can be a single layer of a liquid impermeable material, such as a polymeric film. In an embodiment, the outer cover 26 can be suitably stretchable, and more suitably elastic, in at least the lateral direction 32 of the absorbent article 10. In an embodiment, the outer cover 26 can be stretchable, and more suitably elastic, in both the lateral 32 and the longitudinal directions. In an embodiment, the outer cover 26 can be a multi-layered laminate in which at least one of the layers is liquid impermeable. In some embodiments, the outer cover 26 can be a two-layer construction, including an outer layer (not shown) and an inner layer (not shown) which can be bonded together such as by a laminate adhesive. Suitable laminate adhesives can be applied continuously or intermittently as beads, a spray, parallel swirls, or the like, but it is to be understood that the inner layer can be bonded to the outer layer by other bonding methods, including, but not limited to, ultrasonic bonds, thermal bonds, pressure bonds, or the like.

The outer layer of the outer cover 26 can be any suitable material and may be one that provides a generally cloth-like texture or appearance to the wearer. An example of such material can be a 100% polypropylene bonded-carded web with a diamond bond pattern available from Sandler A.G., Germany, such as 30 gsm Sawabond 4185® or equivalent. Another example of material suitable for use as an outer layer of an outer cover 26 can be a 20 gsm spunbond polypropylene non-woven web. The outer layer may also be constructed of the same materials from which the bodyside liner 28 can be constructed as described herein.

The liquid impermeable inner layer of the outer cover 26 (or the liquid impermeable outer cover 26 where the outer cover 26 is of a single-layer construction) can be either vapor permeable (i.e., "breathable") or vapor impermeable. The liquid impermeable inner layer (or the liquid impermeable outer cover 26 where the outer cover 26 is of a single-layer construction) can be manufactured from a thin plastic film. The liquid impermeable inner layer (or the liquid impermeable outer cover 26 where the outer cover 26 is of a single-layer construction) can inhibit liquid body exudates from leaking out of the absorbent article 10 and wetting articles, such as bed sheets and clothing, as well as the wearer and caregiver.

In some embodiments, where the outer cover 26 is of a single layer construction, it can be embossed and/or matte finished to provide a more cloth-like texture or appearance. The outer cover 26 can permit vapors to escape from the absorbent article 10 while preventing liquids from passing through. A suitable liquid impermeable, vapor permeable material can be composed of a microporous polymer film or a non-woven material which has been coated or otherwise treated to impart a desired level of liquid impermeability.

Absorbent Body:

The absorbent body 34 can be suitably constructed to be generally compressible, conformable, pliable, non-irritating to the wearer's skin and capable of absorbing and retaining liquid body exudates. The absorbent body 34 can be manufactured in a wide variety of sizes and shapes (for example, rectangular, trapezoidal, T-shape, I-shape, hourglass shape, etc.) and from a wide variety of materials. The size and the absorbent capacity of the absorbent body 34 should be compatible with the size of the intended wearer (infants to adults) and the liquid loading imparted by the intended use of the absorbent article 10. The absorbent body 34 can have a length and width that can be less than or equal to the length and width of the absorbent article 10.

In an embodiment, the absorbent body 34 can be composed of a web material of hydrophilic fibers, cellulosic fibers (e.g., wood pulp fibers), natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In an embodiment, the absorbent body 34 can be a matrix of cellulosic fluff and superabsorbent material. In further embodiments, the absorbent body 34 can comprise mostly superabsorbent material, or even greater than 80% superabsorbent material, greater than 90% superabsorbent material, or comprise 100% superabsorbent material, by weight of absorbent material of the absorbent body 34. Although, in other embodiments, the absorbent body 34 can be free of superabsorbent material. In an embodiment, the absorbent body 34 may be constructed of a single layer of materials, or in the alternative, may be constructed of two or more layers of materials.

Various types of wettable, hydrophilic fibers can be used in the absorbent body 34. Examples of suitable fibers include natural fibers, cellulosic fibers, synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers, or composed of nonwettable thermoplastic polymers, such as polyolefin fibers which have been hydrophilized by suitable means. The fibers may be hydrophilized, for example, by treatment with a surfactant, treatment with silica, treatment with a material which has a suitable hydrophilic moiety and is not readily removed from the fiber, or by sheathing the nonwettable, hydrophobic fiber with a hydrophilic polymer during or after formation of the fiber. Suitable superabsorbent materials can be selected from natural, synthetic, and modified natural polymers and materials. The superabsorbent materials can be inorganic materials, such as silica gels, or organic compounds, such as cross-linked polymers.

If a spacer layer is present, the absorbent body 34 can be disposed on the spacer layer and superposed over the outer cover 26. The spacer layer can be bonded to the outer cover 26, for example, by adhesive. In some embodiments, a spacer layer may not be present and the absorbent body 34 can directly contact the outer cover 26 and can be directly bonded to the outer cover 26. However, it is to be understood that the absorbent body 34 may be in contact with, and not bonded with, the outer cover 26 and remain within the scope of this disclosure. In an embodiment, the outer cover 26 can be composed of a single layer and the absorbent body 34 can be in contact with the singer layer of the outer cover 26. In some embodiments, at least a portion of a layer, such as but not limited to, a fluid transfer layer and/or a spacer layer, can be positioned between the absorbent body 34 and the outer cover 26. The absorbent body 34 can be bonded to the fluid transfer layer and/or the spacer layer.

Bodyside Liner:

The bodyside liner 28 of the absorbent article 10 can overlay the absorbent body 34 and the outer cover 26 and can isolate the wearer's skin from liquid waste retained by the absorbent body 34. In various embodiments, a fluid transfer layer can be positioned between the bodyside liner 28 and the absorbent body 34. In various embodiments, an acquisition layer (not shown) can be positioned between the bodyside liner 28 and the absorbent body 34 or a fluid transfer layer, if present. In various embodiments, the bodyside liner 28 can be bonded to the acquisition layer, or to the fluid transfer layer if no acquisition layer is present, via adhesive and/or by a point fusion bonding. The point fusion bonding may be selected from ultrasonic, thermal, pressure bonding, and combinations thereof.

In an embodiment, the bodyside liner 28 can extend beyond the absorbent body 34 and/or a fluid transfer layer, if present, and/or an acquisition layer, if present, and/or a spacer layer, if present, to overlay a portion of the outer cover 26 and can be bonded thereto by any method deemed suitable, such as, for example, by being bonded thereto by adhesive, to substantially enclose the absorbent body 34 between the outer cover 26 and the bodyside liner 28. It is contemplated that the bodyside liner 28 may be narrower than the outer cover 26. However, in other embodiments, the bodyside liner 28 and the outer cover 26 may be of the same dimensions in width and length, for example, as can be seen in the embodiments illustrated in FIG. 1. In other embodiments, the bodyside liner 28 can be of greater width than the outer cover 26. It is also contemplated that the bodyside liner 28 may not extend beyond the absorbent body 34 and/or may not be secured to the outer cover 26. In some embodiments, the bodyside liner 28 can wrap at least a portion of the absorbent body 34, including wrapping around both longitudinal edges 36, 38 of the absorbent body 34, and/or one or more of the end edges 40, 42. It is further contemplated that the bodyside liner 28 may be composed of more than one segment of material. The bodyside liner 28 can be of different shapes, including rectangular, hourglass, or any other shape. The bodyside liner 28 can be suitably compliant, soft feeling, and non-irritating to the wearer's skin and can be the same as or less hydrophilic than the absorbent body 34 to permit body exudates to readily penetrate through to the absorbent body 34 and provide a relatively dry surface to the wearer.

The bodyside liner 28 can be manufactured from a wide selection of materials, such as synthetic fibers (for example, polyester or polypropylene fibers), natural fibers (for example, wood or cotton fibers), a combination of natural and synthetic fibers, porous foams, reticulated foams, apertured plastic films, or the like. Examples of suitable materials include, but are not limited to, rayon, wood, cotton, polyester, polypropylene, polyethylene, nylon, or other heat-bondable fibers, polyolefins, such as, but not limited to, copolymers of polypropylene and polyethylene, linear low-density polyethylene, and aliphatic esters such as polylactic acid, finely perforated film webs, net materials, and the like, as well as combinations thereof.

Various woven and non-woven fabrics can be used for the bodyside liner 28. The bodyside liner 28 can include a woven fabric, a nonwoven fabric, a polymer film, a film-fabric laminate or the like, as well as combinations thereof. Examples of a nonwoven fabric can include spunbond fabric, meltblown fabric, coform fabric, carded web, bonded-carded web, bicomponent spunbond fabric, spunlace, or the like, as well as combinations thereof. The bodyside liner 28 need not be a unitary layer structure, and thus, can include more than one layer of fabrics, films, and/or webs, as well as combinations thereof. For example, the bodyside liner 28 can include a support layer and a projection layer that can be hydroentagled. The projection layer can include hollow projections, such as those disclosed in U.S. Pat. No. 9,474,660 to Kirby, Scott S. C. et al.

For example, the bodyside liner 28 can be composed of a meltblown or spunbond web of polyolefin fibers. Alternatively, the bodyside liner 28 can be a bonded-carded web composed of natural and/or synthetic fibers. The bodyside liner 28 can be composed of a substantially hydrophobic material, and the hydrophobic material can, optionally, be treated with a surfactant or otherwise processed to impart a desired level of wettability and hydrophilicity. The surfactant can be applied by any conventional means, such as spraying, printing, brush coating or the like. The surfactant can be applied to the entire bodyside liner 28 or it can be selectively applied to particular sections of the bodyside liner 28.

In an embodiment, a bodyside liner 28 can be constructed of a non-woven bicomponent web. The non-woven bicomponent web can be a spunbonded bicomponent web, or a bonded-carded bicomponent web. An example of a bicomponent staple fiber includes a polyethylene/polypropylene bicomponent fiber. In this particular bicomponent fiber, the polypropylene forms the core and the polyethylene forms the sheath of the fiber. Fibers having other orientations, such as multi-lobe, side-by-side, end-to-end may be used without departing from the scope of this disclosure. In an embodiment, a bodyside liner 28 can be a spunbond substrate with a basis weight from about 10 or 12 to about 15 or 20 gsm. In an embodiment, a bodyside liner 28 can be a 12 gsm spunbond-meltblown-spunbond substrate having 10% meltblown content applied between the two spunbond layers.

Although the outer cover 26 and bodyside liner 28 can include elastomeric materials, it is contemplated that the outer cover 26 and the bodyside liner 28 can be composed of materials which are generally non-elastomeric. In an embodiment, the bodyside liner 28 can be stretchable, and more suitably elastic. In an embodiment, the bodyside liner 28 can be suitably stretchable and more suitably elastic in at least the lateral or circumferential direction of the absorbent article 10. In other aspects, the bodyside liner 28 can be stretchable, and more suitably elastic, in both the lateral and the longitudinal directions 32, 30, respectively.

Containment Flaps:

In an embodiment, the absorbent article 10 can include a pair of containment flaps 50, 52. The containment flaps 50, 52 can be formed separately from the absorbent chassis 11 and attached to the chassis 11 or can be formed integral to the chassis 11. In some embodiments, the containment flaps 52 can be secured to the chassis 11 of the absorbent article 10 in a generally parallel, spaced relation with each other laterally inward of the leg openings to provide a barrier against the flow of body exudates. One containment flap 50 can be on a first side of the longitudinal axis 29 and the other containment flap 52 can be on a second side of the longitudinal axis 29. In an embodiment, the containment flaps 50, 52 can extend generally in a longitudinal direction 30 from the front waist region 12 of the absorbent article 10 through the crotch region 16 to the rear waist region 14 of the absorbent article 10. In some embodiments, the containment flaps 50, 52 can extend in a direction substantially parallel to the longitudinal axis 29 of the absorbent article 10, however, in other embodiments, the containment flaps 50, 52 can be curved, as is known in the art.

In embodiments where the containment flaps 50, 52 are coupled to the chassis 11, the containment flaps 50, 52 can be bonded to the bodyside liner 28 with a barrier adhesive connecting the projections portion 66 to the body facing surface 19 of the chassis 11, or the containment flaps 50, 52 can be bonded to the outer cover 26 with a barrier adhesive in some embodiments where the bodyside liner 28 does not extend the full lateral width of the outer cover 26. Of course, the containment flaps 50, 52 can be bonded to other components of the chassis 11 and can be bonded with other suitable means other than a barrier adhesive. The containment flaps 50, 52 can be constructed of a fibrous material which can be similar to the material forming the bodyside liner 28. Other conventional materials, such as polymer films, can also be employed.

The containment flaps 50, 52 can each include a base portion 64 and a projection portion 66. The base portion 64 can be bonded to the chassis 11, for example, to the bodyside liner 28 or the outer cover 26 as mentioned above. The base portion 64 can include a proximal end 64a and a distal end 64b. The projection portion 66 can be separated from the base portion 64 at the proximal end 64a of the base portion 64. As used in this context, the projection portion 66 is separated from the base portion 64 at the proximal end 64a of the base portion 64 in that the proximal end 64a of the base portion 64 defines a transition between the projection portion 66 and the base portion 64. The proximal end 64a of the base portion 64 can be located near the barrier adhesive. In some embodiments, the distal ends 64b of the base portion 64 can laterally extend to the respective longitudinal side edges 18, of the absorbent article 10. In other embodiments, the distal ends 64b of the base portion 64 can end laterally inward of the respective longitudinal side edges 18, 20 of the absorbent article 10. The containment flaps 50, 52 can also each include a projection portion 66 that is configured to extend away from the body facing surface 19 of the chassis 11 at least in the crotch region 16 when the absorbent article 10 are in a relaxed configuration. The containment flaps 50, 52 can include a tack-down region 71 in either or both of the front waist region 12 and the rear waist region 14 where the projection portion 66 is coupled to the body facing surface 19 of the chassis 11.

It is contemplated that the containment flaps 50, 52 can be of various configurations and shapes, and can be constructed by various methods. For example, the containment flaps 50, 52 of FIG. 1 depict a longitudinally extending containment flap 50, 52 with a tack-down region 71 in both the front and rear waist regions 12, 14 where the projection portion 66 of each containment flap 50, 52 is tacked down to the bodyside liner 28 towards or away from the longitudinal axis 29 of the absorbent article 10. However, the containment flaps 50, 52 can include a tack-down region 71 where the projection portion 66 of each of the containment flaps 50, 52 is folded back upon itself and coupled to itself and the bodyside liner 28 in a "C-shape" configuration, as is known in the art and described in U.S. Pat. No. 5,895,382 to Robert L. Popp et al.

As yet another alternative, it is contemplated that the containment flaps 50, 52 could be constructed in a "T-shape" configuration, such as described in U.S. Pat. No. 9,259,362 to Robert L. Popp et al. Such a configuration can also include a tack-down region 71 in either or both of the front and rear waist regions 12, 14, respectively. Of course, other configurations of containment flaps 50, 52 can be used in the absorbent article 10 and still remain within the scope of this disclosure.

The containment flaps 50, 52 can include one or more flap elastic members 68, such as the two flap elastic strands depicted in FIG. 1. Suitable elastic materials for the flap elastic members 68 can include sheets, strands or ribbons of natural rubber, synthetic rubber, or thermoplastic elastomeric materials. Of course, while two elastic members 68 are shown in each containment flap 50, 52, it is contemplated that the containment flaps 50, 52 can be configured with one or three or more elastic members 68. Alternatively or additionally, the containment flaps 50, 52 can be composed of a material exhibiting elastic properties itself.

The flap elastic members 68, as illustrated in FIG. 1, can have two strands of elastomeric material extending longitudinally in the projection portion 66 of the containment flaps 50, 52, in generally parallel, spaced relation with each other. The elastic members 68 can be within the containment flaps 50, 52 while in an elastically contractible condition such that contraction of the strands gathers and shortens the projection portions 66 of the containment flaps 50, 52 in the longitudinal direction 30. As a result, the elastic members 68 can bias the projection portions 66 of the containment flaps 50, 52 to extend away from the body facing surface 45 of the absorbent assembly 44 in a generally upright orientation of the containment flaps 50, 52, especially in the crotch region 16 of the absorbent article 10, when the absorbent article 10 is in a relaxed configuration.

During manufacture of the containment flaps 50, 52 at least a portion of the elastic members 68 can be bonded to the containment flaps 50, 52 while the elastic members 68 are elongated. The percent elongation of the elastic members 68 can be, for example, about 110% to about 350%. The elastic members 68 can be coated with adhesive while elongated to a specified length prior to attaching to the elastic members 68 to the containment flaps 50, 52. In a stretched condition, the length of the elastic members 68 which have adhesive coupled thereto can provide an active flap elastic region 70 in the containment flaps 50, 52, as labeled in FIG. 1, which will gather upon relaxation of the absorbent article 10. The active flap elastic region 70 of containment flaps 50, 52 can be of a longitudinal length that is less than the length of the absorbent article 10. In this exemplary method of bonding the elastic members 68 to the containment flaps 50, 52, the portion of the elastic members 68 not coated with adhesive will retract after the elastic members 68 and the absorbent article 10 are cut in manufacturing to form an individual absorbent article 10. As noted above, the relaxing of the elastic members 68 in the active flap elastic region 70 when the absorbent article 10 is in a relaxed condition can cause each containment flap 50, 52 to gather and cause the projection portion 66 of each containment flap 50, 52 to extend away from the body facing surface 19 of the chassis 11 (e.g., the body facing surface 45 of the absorbent assembly 44 or the body facing surface 56 of the bodyside liner 28).

Of course, the elastic members 68 can be bonded to the containment flaps 50, 52 in various other ways as known by those of skill in the art to provide an active flap elastic region 70, which is within the scope of this disclosure. Additionally, the active flap elastic regions 70 can be shorter or longer than depicted herein, including extending to the front waist edge 22 and the rear waist edge 24, and still be within the scope of this disclosure.

Leg Elastics:

Leg elastic members 60, 62 can be secured to the outer cover 26, such as by being bonded thereto by laminate adhesive, generally laterally inward of the longitudinal side edges, 18 and 20, of the absorbent article 10. The leg elastic members 60, 62 can form elasticized leg cuffs that further help to contain body exudates. In an embodiment, the leg elastic members 60, 62 may be disposed between inner and outer layers (not shown) of the outer cover 26 or between other layers of the absorbent article 10, for example, between the base portion 64 of each containment flap 50, 52 and the bodyside liner 28, between the base portion 64 of each containment flap 50, 52 and the outer cover 26, or between the bodyside liner 28 and the outer cover 26. The leg elastic members 60, 62 can be one or more elastic components near each longitudinal side edge 18, 20. For example, the leg elastic members 60, 62 as illustrated herein each include two elastic strands. A wide variety of elastic materials may be used for the leg elastic members 60, 62. Suitable elastic materials can include sheets, strands or ribbons of natural rubber, synthetic rubber, or thermoplastic elastomeric materials. The elastic materials can be stretched and secured to a substrate, secured to a gathered substrate, or secured to a substrate and then elasticized or shrunk, for example, with the application of heat, such that the elastic retractive forces are imparted to the substrate. Additionally, it is contemplated that the leg elastic members 60, 62 can be formed with the containment flaps 50, 52, and then attached to the chassis 11 in some embodiments. Of course, the leg elastic members 60, 62 can be omitted from the absorbent article 10 without departing from the scope of this disclosure.

Elasticated Waist Member:

In an embodiment, the absorbent article 10 can have one or more elasticated waist members 54. The elasticated waist member(s) 54 can be disposed in the rear waist region 14 as illustrated in FIG. 1, or in both the rear waist region 14 and the front waist region 12. Although generally described in the present disclosure with reference to a singular elasticated waist member, it should be understood that such description applies equally to each elasticated waist member in embodiments which contain multiple elasticated waist members 54. As will be discussed in more detail below, the elasticated waist member 54 can help contain and/or absorb body exudates, especially low viscosity fecal matter, and as such, can be preferred to be in the rear waist region 14. An elasticated waist member 54 in the front waist region 12 can help contain and/or absorb body exudates, such as urine, in the front waist region 12. Although not as prevalent as in the rear waist region 14, in some circumstances, fecal material may also spread to the front waist region 12, and thus, an elasticated waist member 54 disposed in the front waist region 12 can help contain and/or absorb body exudates as well.

The elasticated waist member 54 can be comprised of a variety of materials. In a preferred embodiment, the elasticated waist member 54 can be comprised of a spunbond-meltblown-spunbond ("SMS") material. However it is contemplated that the elasticated waist member 54 can be comprised of other materials including, but not limited to, a spunbond-film-spunbond ("SFS"), a bonded carded web ("BOW"), or any non-woven material. In some embodiments, the elasticated waist member 54 can be comprised of a laminate of more than one of these exemplary materials, or other materials. In some embodiments, the elasticated waist member 54 can be comprised of a liquid impermeable material, for example a film material. In some embodiments, the elasticated waist member 54 can be comprised of a material coated with a hydrophobic coating. The basis weight of the material forming the elasticated waist member 54 can vary, however, in a preferred embodiment, the basis weight can be between about 8 gsm to about 120 gsm, not including the elastic members 86 in the elasticated waist member 54. More preferably, the basis weight of the material comprising the elasticated waist member 54 can be between about 10 gsm to about 40 gsm, and even more preferably, between about 15 gsm to about 25 gsm.

The elasticated waist member 54 can include a first longitudinal side edge 72, a second longitudinal side edge 74, a waist member first end edge and a waist member second end edge joining the first longitudinal edge 72 and the second longitudinal edge 74. The first longitudinal side edge 72 can be opposite from the second longitudinal side edge 74. The distance between the first longitudinal side edge 72 and the second longitudinal side edge 74 can define a width of the elasticated waist member 54 in the lateral direction 32. Although not depicted, in some embodiments, the first longitudinal side edge 72 can substantially align with the first longitudinal side edge 18 of the absorbent article 10. Similarly, in some embodiments, the second longitudinal side edge 74 can align with the second longitudinal side edge 20 of the absorbent article 10. As illustrated in FIG. 1, the elasticated waist member 54 can be configured such that the first longitudinal side edge 72 can be disposed laterally outward of the proximal end 64a of the base portion 64 of the containment flap 50. Similarly, the elasticated waist member 54 can be configured such that the second longitudinal side edge 74 can be disposed laterally outward of the proximal end 64a of the base portion 64 of the containment flap 52.

In preferred embodiments, the elasticated waist member 54 can include at least one elastic member 86. In some embodiments, the elasticated waist member 54 can include multiple elastic members 86, such as five elastic members 86. Of course, it is contemplated that the elasticated waist member 54 can include other amounts of elastic members 86, such as three, four, six, eight, or ten elastic members, and in some embodiments, no elastic members 86. The elastic member 86 can span substantially from the first longitudinal side edge 72 to the second longitudinal side edge 74 of the elasticated waist member 54. In some embodiments, the elastic members 86 can be spaced evenly in the longitudinal direction 30. At least one of the elastic members 86 can be disposed located near the waist member second end edge of the elasticated waist member 54.

A wide variety of elastic materials may be used for the elastic member(s) 86 in the elasticated waist member 54. Suitable elastic materials can include sheets, strands or ribbons of natural rubber, synthetic rubber, thermoplastic elastomeric materials, or elastic foams. The elastic materials can be stretched and secured to a substrate forming the elasticated waist member 54, secured to a gathered substrate, or secured to a substrate and then elasticized or shrunk, for example, with the application of heat, such that the elastic retractive forces are imparted to the substrate forming the elasticated waist member 54.

In some embodiments, the elasticated waist member 54 can be disposed on the body facing surface 45 of the absorbent assembly 44. In some embodiments, such as in embodiments illustrated in FIG. 1, the elasticated waist member 54 can be disposed on the body facing surface 56 of the bodyside liner 28.

In various embodiments, the elasticated waist member 54 can also include a proximal portion (not shown) and a distal portion (not shown). The proximal portion can be coupled to the body facing surface 19 of chassis 11 (e.g., the body facing surface 45 of the absorbent assembly 44 or the body facing surface 56 of the bodyside liner 28) whereas the distal portion or at least a portion of the distal portion of the elasticated waist member 54 can be free to move with respect to the chassis 11 and the absorbent assembly 44 when the absorbent article 10 is in the relaxed configuration. A first fold (not shown) can separate the proximal portion from the distal portion in the various embodiments of the elasticated waist member 54 discussed herein. As used in this context, the first fold separates the proximal portion from the distal portion in that the first fold defines a transition between the proximal portion and the distal portion in the containment member material and the containment member 54 as a whole. In alternate embodiments (not shown) the proximal portion and the distal portion can be made from separate materials which are attached to one another such as, for example, in the area of the first fold or in lieu of the first fold. The physical form of the attachment may be, for example, by way of a butt seam or a lap seam.

The proximal portion of such an elasticated waist member 54 can be coupled to the body facing surface 19 of the chassis 11 with an adhesive, and in some embodiments, the proximal portion can be coupled to the body facing surface 45 of the absorbent assembly 44. In some embodiments, the proximal portion of the elasticated waist member 54 can be coupled to the body facing surface 56 of the bodyside liner 28. However, in some embodiments, the proximal portion of the elasticated waist member 54 can be coupled to the body facing surface 58 of the rear waist panel 15. The proximal portion can be coupled to the body facing surface 45 of the absorbent assembly 44 with adhesive along the entire length of the proximal portion in the longitudinal direction 30. However, it can be contemplated that only a portion of the proximal portion in the longitudinal direction 30 is coupled to the body facing surface 45 of the absorbent assembly 44. Of course, it is contemplated that the proximal portion of the elasticated waist member 54 can be coupled to the body facing surface 19 of the chassis 11 or the body facing surface 45 of the absorbent assembly 44 by means other than an adhesive, such as by pressure bonding, ultrasonic bonding, thermal bonding, and combinations thereof. In preferred embodiments, the proximal portion is coupled to the body facing surface 19 of the chassis 11 in the lateral direction 32 in a constant fashion along the lateral axis 31, as opposed to an intermittent fashion, such that a barrier to body exudates is formed between the proximal portion and the body facing surface 19 of the chassis 11.

The proximal portion of the elasticated waist member 54 can include a longitudinal length measured in the longitudinal direction 30 along the longitudinal axis 29 that is shorter than a longitudinal length of the distal portion of the elasticated waist member 54 (not shown). However in some embodiments, the longitudinal length of the proximal portion can be substantially equal to or larger than the longitudinal length of the distal portion of the elasticated waist member 54. It can be appreciated that the relative longitudinal lengths of the proximal portion and the distal portion can be varied between embodiments of the elasticated waist member 54 without departing from the scope of this disclosure.

In such embodiments of an elasticated waist member 54, because the distal portion of the elasticated waist member 54 can freely move with respect to the absorbent assembly 44 when the absorbent article 10 is in the relaxed configuration, the distal portion can help provide a containment pocket when the absorbent article 10 is in the relaxed configuration when being worn by the wearer. The containment pocket can help provide a barrier to contain and/or can help absorb body exudates. The first longitudinal side edge 72 can be disposed laterally outward of the proximal end 64a of the base portion 64 of the containment flap 50, and thus, the pocket can extend laterally outward of the proximal end 64a of the containment flap 50. Similarly, the second longitudinal side edge 74 can be disposed laterally outward of the proximal end 64a of the base portion 64 of the containment flap 52 and the pocket can extend laterally outward of the proximal end 64a of the containment flap 52. Such a configuration provides elasticated waist member 54 with a wide containment pocket to contain and/or absorb body exudates. To help prevent lateral flow of body exudates that are contained by the containment pocket of the elasticated waist member 54, the distal portion of the elasticated waist member 54 can be bonded to the proximal portion of the elasticated waist member 54 and/or the body facing surface 19 of the chassis 11 near the first and second longitudinal side edges 72, 74, respectively. For example, FIG. 1 depicts tack-down regions 84 where the distal portion of the elasticated waist member 54 can be bonded to the proximal portion of the elasticated waist member 54 and/or the body facing surface 19 of the chassis 11 near the first and second longitudinal side edges 72, 74, respectively.

As depicted in FIG. 1, in some embodiments the elasticated waist member 54 can be disposed on the body facing surface 19 of the chassis 11 such that a gap is provided between the second end edge 42 of the absorbent body 34 and the waist member second end edge of the distal portion of the elasticated waist member 54. By providing a gap, the containment can have a greater void volume for body exudates. Additionally, it is believed that gap can help body exudates enter the containment pocket of the elasticated waist member 54.

The elasticated waist member 54 can be disposed to be coupled to the chassis 11 by being placed either over the containment flaps 50, 52 or under the containment flaps 50, 52. More specifically, as shown in FIG. 1, the elasticated waist member 54 can be disposed on the body facing surface 19 of the chassis 11 such that the proximal portion of the elasticated waist member 54 is disposed over the base portion 64 of the first and the second containment flaps 50, 52, respectively. Alternatively, the elasticated waist member 54 can be disposed on the body facing surface 19 of the chassis 11 such that the proximal portion of the elasticated waist member 54 is disposed under the base portion 64 of the first and the second containment flaps 50, 52, respectively. Both configurations can provide advantages to the functioning of the elasticated waist member 54 to contain and/or absorb body exudates.

Embodiments where the proximal portion of the elasticated waist member 54 is disposed over the base portion 64 of the containment flaps 50, 52 can provide the advantage that the containment flaps 50, 52 can help the distal portion of the elasticated waist member 54 extend away from the body facing surface 45 of the absorbent assembly 44 when the absorbent article 10 is applied to the wearer. This is especially relevant where the proximal portion of the elasticated waist member 54 has a shorter longitudinal length than the distal portion of the elasticated waist member 54.

For example, because the proximal portion is shorter than the distal portion, the flap elastics 68 in the projection portion 66 of the containment flaps 50, 52 can provide an opening force on the distal portion of the elasticated waist member 54 when the absorbent article 10 is in the relaxed configuration and applied to the wearer, thus helping the distal portion extend away from the body facing surface 45 of the absorbent assembly 44 and opening the containment pocket. In some embodiments, the containment pocket can be additionally or alternatively opened by configuring the containment flaps 50, 52 to have an active flap elastic region 70 that longitudinally overlaps with the distal portion of the elasticated waist member 54 when the absorbent article 10 is in the stretched, laid flat configuration, such as illustrated in FIG. 1. Additionally or alternatively, the containment pocket of the elasticated waist member 54 can be opened by configuring the containment flaps 50, 52 to have a tack-down region 71 that does not extend to a distal edge of the distal portion of the elasticated waist member 54, such as illustrated in FIG. 1. However, such a configuration of the tack-down region 71 is not required, and in some embodiments, the tack-down region 71 can extend from the rear waist edge 24 past the distal edge of the distal portion of the elasticated waist member 54.

Embodiments where the proximal portion of the elasticated waist member 54 is disposed under the base portion 64 of the containment flaps 50, 52 can provide the advantage of having the containment pocket formed by the elasticated waist member 54 be free from the projection portion 66 of the containment flaps 50, 52. Both the base portion 64 and the projection portion 66 of each containment flap 50, 52 can be coupled to the body facing surface 55 of the elasticated waist member 54. As a result, body exudates may more freely spread through the full width of the containment pocket created by the elasticated waist member 54. Additionally, the coupling of the base portion 64 of the containment flaps 50, 52 to the outer cover 26 (or in some embodiments to the bodyside liner 28) can create a longitudinal barrier to the flow of body exudates out of the containment pocket for exudates that spread laterally beyond the location of a barrier adhesive connecting the projection portion 66 of the flaps 50, 52 to the body facing surface 19 of the chassis 11. In some embodiments, the tack-down region 71 of the projection portion 66 of each of the containment flaps 50, 52 can longitudinally overlap with the distal portion of the elasticated waist member 54. In some embodiments, the tack-down region 71 of projection portion 66 of each of the containment flaps 50, 52 can extend to the distal edge of the elasticated waist member 54 to further assist in containing exudates within the containment pocket created by the elasticated waist member 54.

Fastening System:

In an embodiment, the absorbent article 10 can include a fastening system. The fastening system can include one or more back fasteners 91 and one or more front fasteners 92. The embodiments being shown in FIG. 1 depict embodiments with one front fastener 92. Portions of the fastening system may be included in the front waist region 12, rear waist region 14, or both.

The fastening system can be configured to secure the absorbent article 10 about the waist of the wearer in a fastened condition and help maintain the absorbent article 10 in place during use. In an embodiment, the back fasteners 91 can include one or more materials bonded together to form a composite ear as is known in the art. For example, the composite fastener may be composed of a stretch component 94, a nonwoven carrier or hook base 96, and a fastening component 98, as labeled in FIG. 1. In some embodiments the elasticated waist member 54 can laterally extend to the back fasteners 91, and/or to each of the longitudinal side edges 18, 20 of the absorbent article 10. In some embodiments, the elasticated waist member 54 can be coupled to the stretch component 94 of the back fasteners 91, either directly or indirectly.

Apertured Region:

According to some embodiments of the present disclosure, bodyside liner 28 of the article 10 may further comprise one or more apertures 27, for example as indicated at apertured region 25. The apertures 27 can help body exudates transfer through the bodyside liner 28 into interior portions of the article 10 where the exudates are stored and disposed away from a wearer's skin. Portions of the bodyside liner 28 including the apertures 27 may be particularly suited to transferring and trapping low-viscosity fecal matter away from a wearer's skin. Such an effect may help to maintain comfort and skin health of a wearer by preventing prolonged contact between the fecal matter and the wearer's skin. Conversely, portions of the bodyside liner 28 including the apertures 27, or other relatively large apertures, may be less desirable for management of urine exudate. For example, where apertures 27 are large enough or plentiful enough to provide a relatively large open area of the liner 28, such apertures 27 provide an avenue for urine to seep back to the body facing surface 19 of the article 10 and thus in contact with a wearer's skin—potentially causing discomfort and/or skin health issues.

Accordingly, in at least some embodiments, the apertured region 25 may be disposed in a localized region of the article 10, as shown in FIG. 1. For example, the apertured region 25 may have a longitudinal extent that is less than the longitudinal extent of the article 10. More specifically, the apertured region 25 may have a longitudinal extent that is less half, or less than a third, or less than a quarter, of the longitudinal extent of the article 10. Additionally, the apertured region 25 may have a lateral extent that is less than the lateral extent of the article 10. In some of these embodiments, the apertured region 25 may be disposed wholly between proximal ends 64a of base portions 64 of the containment flaps 50, 52. In some embodiments, the apertured region 25 may be located wholly within the crotch region 16. In other embodiments, the apertured region 25 may be located wholly within the rear waist region 14. In still further embodiments, the apertured region 25 may span both a portion of the crotch region 16 and the rear waist region 14. The crotch region 16 and the rear waist region 14 are the locations within the article 10 where fecal matter is typically insulted.

In order to ensure that the apertured region 25 is located within a desired region of the article a registration system can be used to determine an alignment of the apertured region 25 and adjust the manufacturing process to modify an alignment of the apertured region 25 with respect to the article 10. Such a registration system can be useful where the bodyside liner material 28 is a full-length material—that is a material which extends for a full length of the absorbent article—or where the bodyside liner material 28 is a cut-and-placed material which has a longitudinal extent less than the longitudinal extent of the article 10, as will be described in more detail below.

Figure 2:
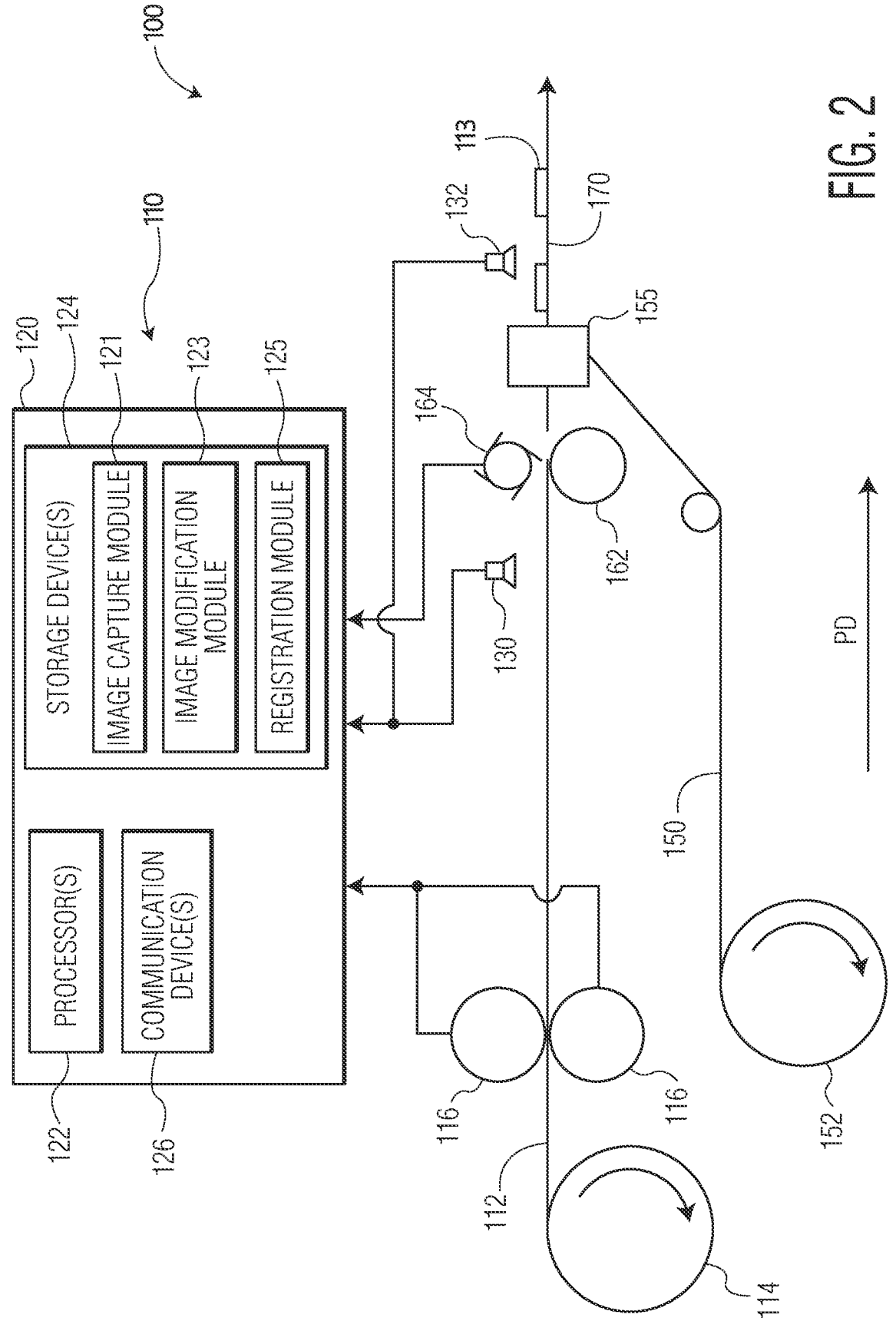
FIG. 2 is a process schematic depicting a manufacturing method including a registration process for registering a first web and a second web, according to aspects of the present disclosure.

FIG. 2 is a schematic diagram of a manufacturing process 100 whereby a first web, such as apertured web material 112, is combined with a secondary web, for example chassis web 150, in a registered manner and further detailing portions of a registration system 110 that may be used as part of the manufacturing process 100. Such a manufacturing process 100 can be used as part of a larger manufacturing process to produce absorbent articles comprising zoned, or localized, apertured webs whereby apertured regions are located at discrete portions of the apertured webs, such as those described with respect to article 10.

Process 100 may include supplying or feeding a continuous first web, such as apertured web material 112, in the process direction PD from a supply roll 114. The continuous web of apertured material 112 may comprise a series of apertured regions, for example similar to apertured region 25 as depicted in FIG. 1 (and also indicated as region 304 in FIG. 5), spaced from each other in the PD. According to some embodiments, the continuous web of apertured material 112 may form a topsheet or topical surge layer of an absorbent article, such as article 10. Accordingly, in at least these embodiments, the continuous web of apertured material 112 may be formed of any of the materials described with respect to bodyside liner 28. However, it should be understood that aspects of the present disclosure, particularly related to registration of continuous web of apertured material 112, can be applied to any apertured material which may be used as any layer within an article, such as article 10.

Process 100 further includes feed or drive rolls 116. Feed rolls 116 assist at least in feeding the continuous web of apertured material 112 in the PD. A rotational speed of feed rolls 116 may be adjusted to speed up or slow down the rate at which the continuous web of apertured material 112 is fed in the process direction. In this manner, the process 100 can affect a change in position of the apertured regions of the continuous web of apertured material 112 with respect to blades of knife roll 164, as will be described in more detail below, to adjust a location on the continuous web of apertured material 112 where the knife roll 164 severs the continuous web of apertured material 112. As can be understood, changing the location where the continuous web of apertured material 112 is severed changes a location of the cut relative to the apertured regions of the continuous web of apertured material 112, thereby affecting the registration of the apertured regions of the continuous web of apertured material 112 with respect to the chassis web 150.

In some embodiments, the system which feeds the continuous web of apertured material 112 in the PD may comprise further components, such as an unwind, an accumulator, and/or a dancer roll, or the like (none of which are shown). Accordingly, it should be understood that the present disclosure contemplates apparatuses and methods for feeding the continuous web of apertured material 112 in the process direction PD which are alternatives, or additions, to feed rolls 116. In whatever form the apparatus(es) and process takes for feeding the continuous web of apertured material 112 in the process direction PD, such apparatus(es) and process typically includes a mechanism for modulating the infeed speed of the continuous web of apertured material 112—that is, the slowing down or speeding up of the speed at which the continuous web of apertured material 112 is fed in the process direction PD. In still further embodiments, rather than adjusting the rotational speed of the feed rolls 116 to affect a change in position of the apertured regions of the continuous web of apertured material 112 relative to where the continuous web of apertured material 112 is severed, a rotational speed of the knife roll 164 may be adjusted. Still further embodiments contemplate different ways of affecting a change of position of where the continuous web of apertured material 112 is severed relative to the apertured regions—thereby affecting the registration of the apertured regions with respect to the chassis web 150. In general, it should be understood that the particular method in which a change in position of where the continuous web of apertured material 112 is severed relative to the apertured regions is not critical as long as such a function is included.

According to process 100, the continuous web of apertured material 112 is fed to a cutting mechanism comprising knife roll 164 and anvil roll 162. Knife roll 164 and anvil roll 162 are configured to cut the continuous web of apertured material 112 into separate, discrete pieces of apertured material 113. The discrete pieces of apertured material 113 are then coupled to a secondary web, such as chassis web 150. In some embodiments, the chassis web 150 may comprise a continuous chassis web comprising components of absorbent article 10. For example, the chassis web 150 may comprise a liner material, such as where the web of apertured material 112 becomes a topical surge material of the article 10. In other embodiments, the chassis web 150 may comprise a continuous outer cover material. In still further embodiments, the chassis web 150 may comprise a continuous outer cover material with one or more absorbent bodies disposed on the continuous outer cover material. The one or more absorbent bodies may be in the form of a continuous absorbent web or of a series of discrete absorbent webs or bodies separated in the process direction PD. The chassis web 150 may be supplied by supply roll 152 or may alternatively be fed from a different portion of a larger manufacturing process. In at least some embodiments, the process may include an ability to change the speed at which the chassis web 150 moves in the process direction PD.

The process 100 may further comprise a web combiner module 155. The web combiner module 155 may in some embodiments be a cut-and-place module, for example where the discrete pieces of apertured material 113 are shorter than a finished product length. Such a web combiner module 155 may be combined with the knife roll 164 to cut, separate, and combine discrete pieces of apertured material 113 with the chassis web 150 in a spaced apart fashion. Although, in other embodiments, the cutting and separating steps may be disconnected—for example the cutting performed by the knife and anvil rolls 164, 162 and the separating and combining steps performed by the web combiner module 155. In further embodiments, the web combiner module 155 may be nip rolls—for example where the continuous web of apertured material 112 is desired to be a full-length material that spans an entire length of a finished product. In such embodiments, the knife roll 164 and anvil roll 162 may come after the web combiner module 155 and may be configured to cut the combined continuous materials of apertured material 112 and chassis web 150. Although, still other modules are contemplated which are known in the art and which can effect a combining of the apertured material 112 with the chassis web 150.

According to aspects of the present disclosure, the process 100 further includes a registration system 110 that may be used to carry out a registration process for registering the apertured web material 112 and the chassis web 150. The registration system 110 can include a registration processing device 120 which itself may include one or more processors 122, one or more data storage devices 124, and at least one communication device 126. The registration system 110 may further include externally connected devices, such as image capture devices 130, 132 and the system 110 may further be connected at least to feed rolls 116. The one or more processors 122 may be configured to implement functionality and/or process instructions for execution within device 120. The one or more processors 122 may be capable of processing instructions stored in data storage device(s)

124. Examples of processor(s) 122 may include, any one or more of a microprocessor, a controller, a digital signal processor (DSP), an application specific integrated circuit (ASIC), a field-programmable gate array (FPGA), or equivalent discrete or integrated logic circuitry.

The communication device 126 may effect communication between the components and modules of the device 120, as well as any external connected devices such as image capture devices 130, 132 and/or feed rolls 116. Each of components 122, 124, and 126 may be interconnected (physically, communicatively, and/or operatively) for inter-component communications. In some examples, communication channels (not shown) may extend between the components 122, 124, and 126, which may comprise a system bus, a network connection, an inter-process communication data structure, or any other method for communicating data.

Where communication device(s) 126 is included, device 120 may utilize communication device(s) 126 to communicate with external devices via one or more networks, such as one or more wired and/or wireless networks. Communication device(s) 126 may be a network interface card, such as an Ethernet card, an optical transceiver, a radio frequency transceiver, or any other type of device that can send and receive information. Other examples of such network interfaces may include Bluetooth®, 3G and WiFi radios computing devices as well as Universal Serial Bus (USB).

The one or more storage device(s) 124 may be configured to store information within device 120 during operation. Storage device(s) 124, in some examples, is described as a computer-readable storage medium. Storage device(s) 124 can be a temporary memory, meaning that a primary purpose of storage device(s) 124 is not long-term storage. Storage device(s) 124, in some examples, can be a volatile memory, for example random access memories (RAM), dynamic random access memories (DRAM), static random access memories (SRAM), and other forms of volatile memories known in the art. In some examples, storage device(s) 124 is used to store program instructions for execution by processor(s) 122. Storage device(s) 124, in one example, is used by software or applications running on device 120 (e.g., modules 122, 124, and 126) to temporarily store information during program execution.

Storage device(s) 124, in some examples, also include one or more computer-readable storage media. Storage device(s) 124 may be configured to store larger amounts of information than volatile memory. Storage device(s) 124 may further be configured for long-term storage of information. In some examples, storage device(s) 124 include non-volatile storage elements such as magnetic hard discs, optical discs, floppy discs, flash memories, or forms of electrically programmable memories (EPROM) or electrically erasable and programmable (EEPROM) memories.

The one or more data storage device(s) 124 may include one or more modules stored therein which may help to perform the registration function of the system 110, for example an image capture module 121, and image modification module 123, and a registration module 125. Although the modules 121, 123, and 125 are described as carrying out a number of functions of the system 110, the functions attributed to such modules may be implemented in more, fewer, and/or different modules. Additionally, in some examples, the functions may not be distributed between physical or logical modules, but, instead, may be executed by, e.g., processors 122 based on instructions and data stored on storage device(s) 124. Further, although modules 121, 123, and 125 are illustrated as part of storage device(s) 124 in the example of FIG. 2, in other examples, the modules 121, 123, and 125 may be implemented separate from storage device(s) 124 including, e.g., implemented in discrete hardware components configured to carry out the functions attributed to the modules in the examples disclosed herein.

Image capture devices 130, 132 may be configured to capture digital images and communicate such captured images to device 120 for storage in the storage device(s) 124. Image capture devices 130, 132 may be digital devices including at least an optical system comprising a lens arrangement and an image sensor, such as charge-coupled device (CCD) sensor or a complementary metal-oxide-semiconductor (CMOS) sensor or the like. The image capture devices 130, 132 may further comprise a shutter and other components typical of image capture devices. Although not shown, the image capture devices 130, 132 may additionally include illumination devices for illuminating the location or object of which the image capture devices 130, 132 are configured to capture images. In at least some of these embodiments, such illumination devices may be positioned opposite the image capture devices 130, 132, such that the illumination provides a back-lit illumination. For example, such illumination devices may be disposed on an opposite side of the webs 112, 170 with respect to the image capture devices 130, 132 of FIG. 2.

The image capture module 121 may be configured to trigger image capture devices 130, 132 and obtain discrete images of the continuous web of apertured material 112 (from image capture device 130) and a combined web 170, comprising at least a portion of apertured web material 112 and the chassis web 150 (from image capture device 132). The images captured from devices 130, 132 are stored in the storage device(s) 124. The image capture module 121 is generally configured to capture images of the apertured web material 112 and the combined web 170 on a once per product basis, according to methods known in the art. For example, the image capture module 121 may be connected to the feed rolls 116 and may adjust the rate at which it triggers the image capture devices 130, 132 as the speed of the apertured web material 112 is increased or decreased. Additionally, initial setup of the trigger may be performed according to methods known in the art to ensure that the captured images correspond to the portions of the apertured web 112 which are ultimately disposed on a single product. For example, such captured images may be displayed on an output devices, and a manual adjustment of the trigger may be made to ensure proper timing of the image capture trigger. Alternatively, one or more preset parameters may be loaded into image capture module 121 and one or more image processing techniques may be used to determine a feature(s) of the captured images. Comparison of the one or more preset parameters and determined feature(s) of the captured images may be performed and an automatic adjustment of the trigger may be performed by image capture module 121 based on the comparison to ensure proper timing of the image capture trigger.

With the captured images stored in the storage device(s) 124, the image modification module 123 may perform one or more image processing modifications to the stored images. For example, the image modification module 123 may be configured to filter the captured images according to one or more filter parameters. Such a filtering process may help to minimize features of non-interest and highlight features of interest—for example, one or more apertured regions. The image modification module 123 may be further configured to accentuate the features of interest by performing one or more morphological process techniques on the captured images and/or the filtered captured images. In some embodiments, the image modification module 123 may be configured to perform a dilation morphological operation on the captured images and/or the filtered captured images. Such image processing modifications will be described in more detail below with respect to FIGS. 3-8.

Finally, the registration module 125 may be configured to identify features of the modified captured images and to adjust the process 100 to ensure a proper registration of the apertured region(s) of the web material 112 is achieved relative to the chassis web 150. For example, the registration module 125 can be configured to identify or determine one or more apertured regions related to the apertured web material 112 and the combined web 170. According to some embodiments, the registration module 125 is configured to identify one or more features of interest related to the determined apertured region(s) within the modified captured images—for example, a leading edge of the determined apertured region(s). In some embodiments, the registration module 125 is further configured to identify a reference feature on each of the modified captured images of the apertured web material 112 and the combined web 170. Next, the registration module 125 may be configured to determine one or more metrics related to the determined features—such as a difference in locations—and, based on the one or more determined metrics, adjust the system 100 to ensure a proper registration of the apertured region(s) of the web material 112 is achieved relative to the chassis web 150. Further function of the registration module 125 is described below with respect to FIGS. 3-8.

Figure 3:
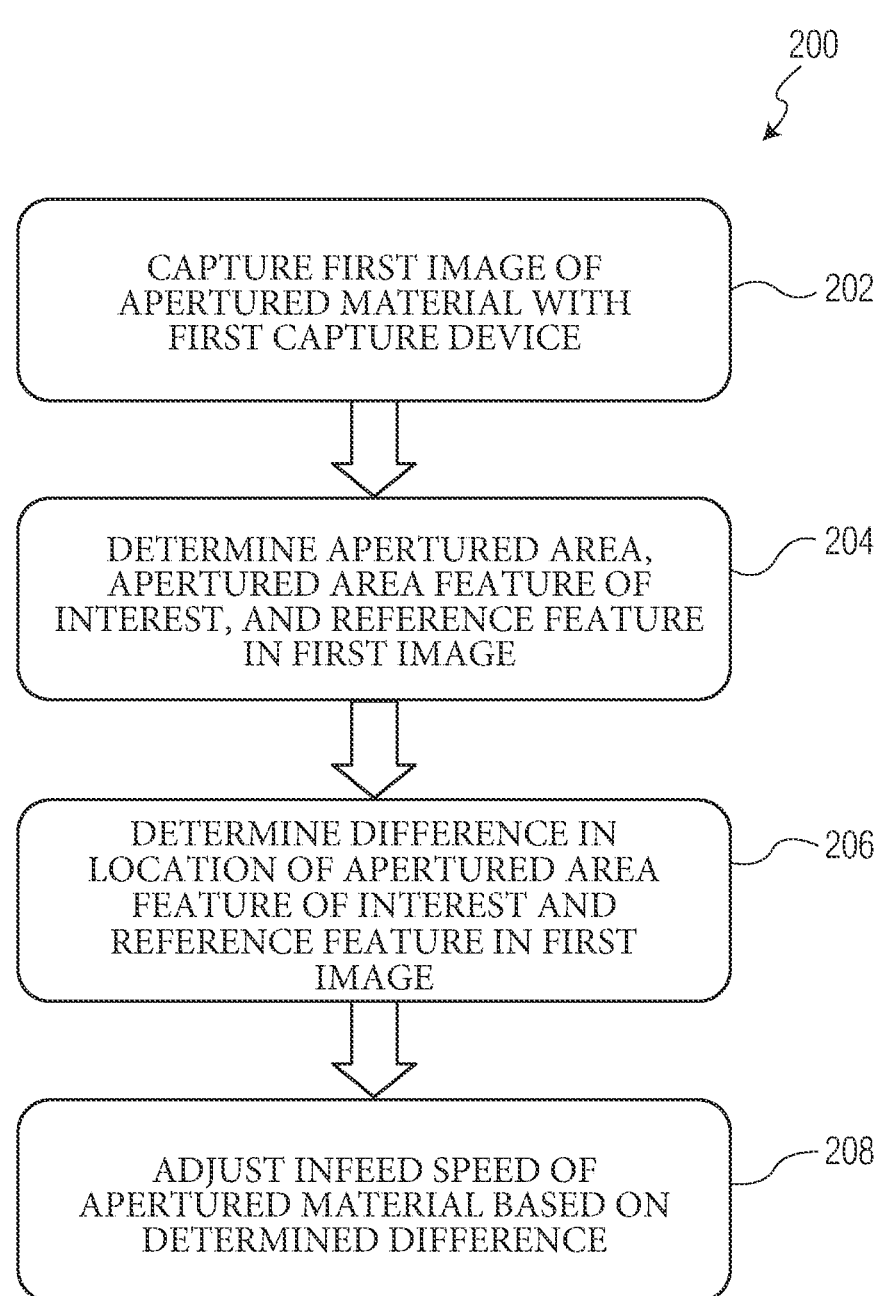
FIG. 3 is a process flow diagram of an exemplary registration method according to aspects of the present disclosure.

FIG. 3 is a process flow diagram of a first exemplary registration process 200 that may be used as part of process 100, for example performed by system 110, for registering the apertured web material 112, and more particularly the apertured region(s) of the apertured web material 112, with the chassis web 150. Process 200 begins with step 202 of capturing a first image of an apertured material. This capturing step may be performed, for example, by image capture module 121 in conjunction with image capture device 130. These first captured images may be communicated by the image capture device 130 to image capture module 121 and stored in the storage device(s) 124.

Figure 5:
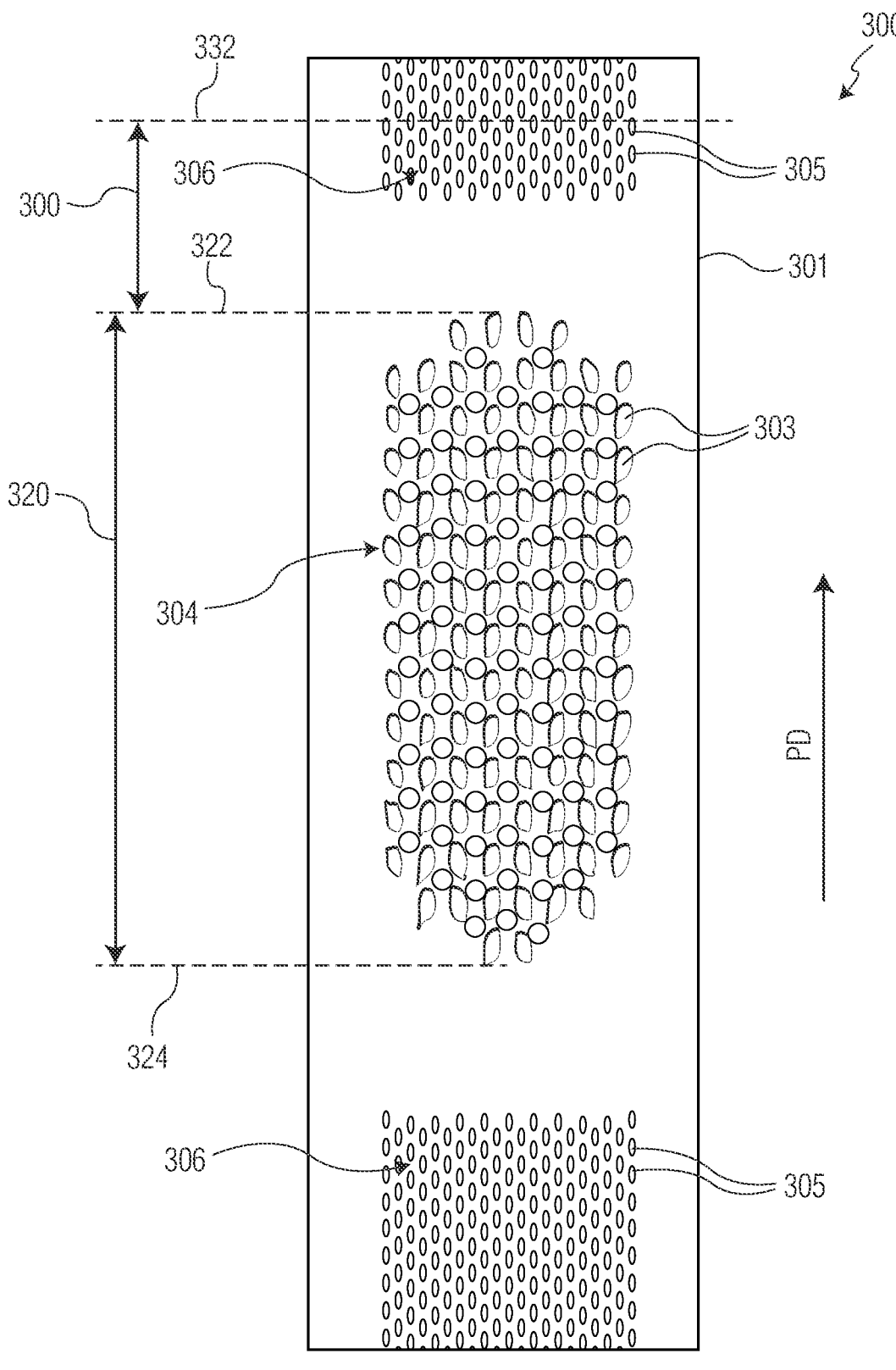
FIG. 5 is a schematic depiction of an exemplary image of an apertured web which may be captured by the manufacturing process of FIG. 2.

FIG. 5 is a schematic depiction of an exemplary first captured image 300 detailing a portion 301 of a continuous, zoned apertured material, which may be representative of apertured web material 112. As can be seen, the portion 301 of the depicted apertured material has a first apertured region 304 comprising relatively large apertures 303. The portion 301 of the depicted apertured material further comprises second apertured regions 306 comprising relatively small apertures 305, with the second apertured regions 306 spaced from the first apertured region 304. In the embodiment of FIG. 5, the first apertured region 304 has a length 320 in the longitudinal direction, which corresponds to the process direction PD as shown, which is less than a total length of the first captured image 300.

Next, as shown at step 204, one or more apertured areas of the first captured image may be determined. For example, the image modification module 123 may modify the first captured image by performing one or more image processing techniques on the first captured image of the apertured web material 112 and may further store the modified first captured image in the storage device(s) 124. In some embodiments, the image modification module 123 may perform one or more morphological image processing techniques. More specifically, image modification module 123 may filter the first captured image to identify or determine all regions of the first captured image which have a light transmittance value equal to or greater than a threshold transmittance value.

Each pixel of the first captured image may have an associated transmittance value—for instance a value on a black to white scale. Typically, such transmittance values, or black/white values, can be determined by averaging the red, blue, and green values associated with each pixel. A lower number represents a darker pixel while a higher number represents a lighter pixel. In the context of the first captured image, the higher a transmittance value, the less material is between the light source and the image capture device. In this manner, the image modification module 123 may be able to determine those pixels falling within open areas of the apertured web material 112. In at least some embodiments, the pixels falling within the filter parameters are assigned a first identification value, such as a one, while those pixels falling outside the filter parameters are assigned a second identification value, such as a zero. In other embodiments, the pixels which fall outside of the filter parameters may have a feature, such as a transmittance or black/white value, set to a first standard number, for example a minimum value, while those pixels which fall within the filter parameters may maintain the values of such feature(s) or may have the value of such feature(s) set to second standard number, such as a maximum value, to distinguish such pixels from the pixels which fell outside of the filter parameters.

In further embodiments, the image modification module 123 may filter the captured image to identify or determine all pixels within regions of the captured image which have a light transmittance value equal to or greater than a threshold transmittance value and which are part of an area having light transmittance values equal to or greater than the threshold transmittance value larger than a threshold area. In some embodiments, the area threshold may be measured in pixels and represents a number of adjacent pixels which have a light transmittance value equal to or greater than a threshold transmittance value. In other embodiments, the area threshold may be a true area having units of $mm^2$ or the like. For example, some particular implementations of the present registration process 200 may be performed by commercially available computer programs coupled to vision and/or registration systems which may automatically compute real world measurements and areas of captured images for use in such filtering operations. In any implementation, these embodiments may be particularly useful where the material of the apertured web material 112 has significant variation in density of the material and/or has additional apertures which are not part of the apertured region(s) desired to be identified. In this manner, the process 200 may filter out, and not identify, portions of the captured image not related to the desired apertured region(s), leaving only the desired apertured region or regions identifiable within the modified captured image.

Figure 6:
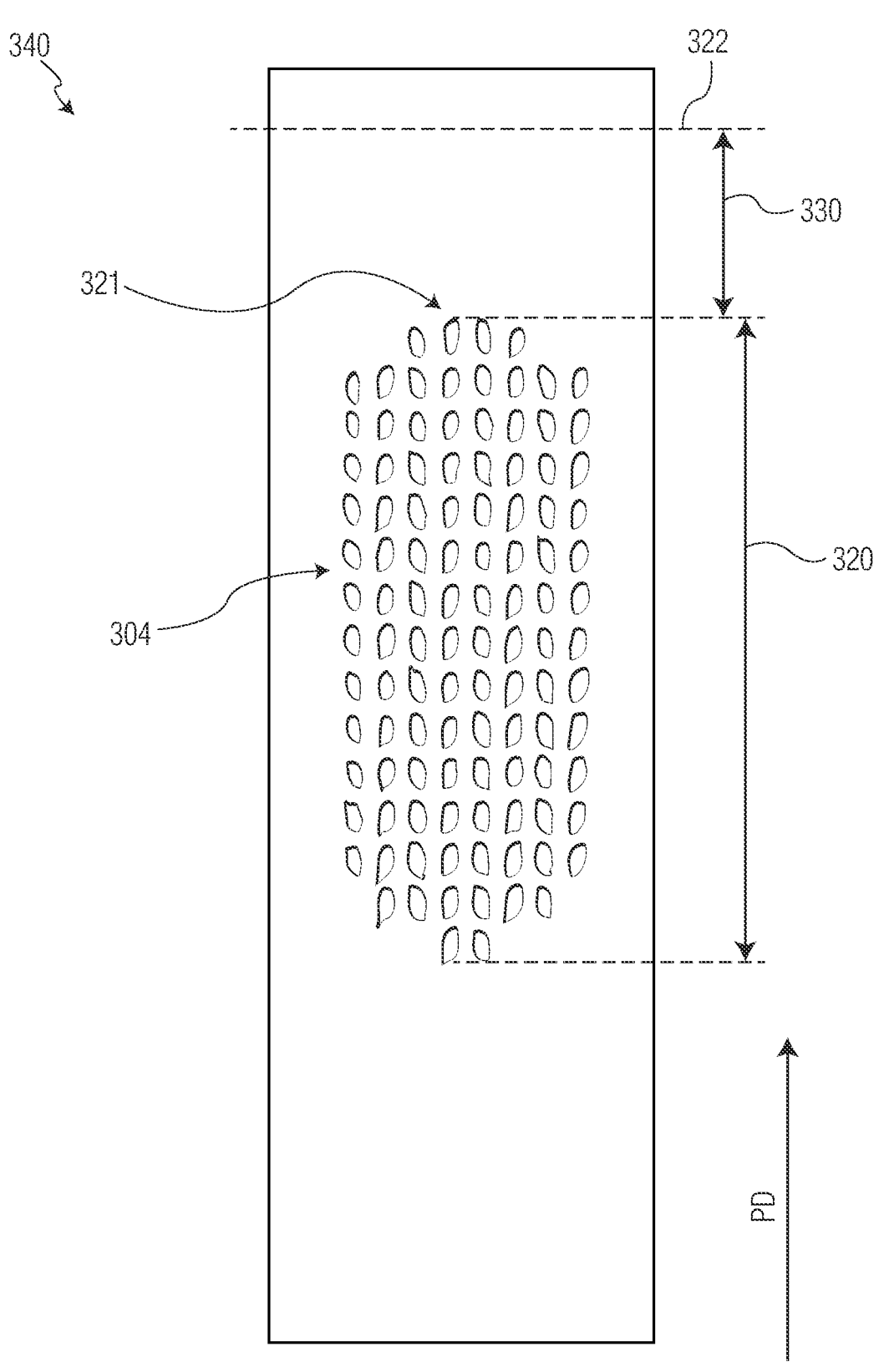
FIG. 6 is a schematic depiction of an exemplary filtered image based on the captured image of FIG. 5 and according to aspects of the present disclosure.

FIG. 6 is an exemplary depiction of a filtered first captured image 340 after the described light transmittance (and optionally area filtering) technique has been performed. As can be seen, the modified first captured image 340 now lacks the second apertured regions 306, leaving only the first apertured region 304 as an identified/determined apertured region.

Next, the image modification module 123 may perform a dilation morphological operation on the filtered first captured image 340, including the identified or determined apertured region(s). In some embodiments, the image modification module 123 may perform multiple dilation morphological operations. Such dilation morphological operations typically expand the boundaries of the identified/determined regions. One exemplary dilation morphological operation may, for each given element (such as an individual pixel) replace each surrounding element with a particular value associated with the given element. In the present process 200, the dilation operation performed by image modification module 123 may, for each pixel having a first identification value, replace the identification value of each surrounding pixel with the first identification value. In this manner, the boundaries of the regions of pixels having the first identification value may expand (e.g. the apertures 303 of the region 304). Although, it should be understood that other dilation operations may be performed which fall within the scope of the present disclosure. For example, rather than assigning each pixel a first or second identification value, instead, the dilation operation may assign the transmittance value of a given identified pixel (e.g. a pixel which met the filtering criteria) to all pixels surrounding the given pixel.

According to some embodiments, the image modification module 123 may perform such a dilation operation until there is only a single, unified aperture (e.g. region of pixels) having the first identification value (or light transmittance values equal to or greater than the threshold transmittance value). In further embodiments, however, the image modification module 123 may perform such a dilation operation until the number of identified discrete, individual apertures having the first identification value (or light transmittance values equal to or greater than the threshold transmittance value) is reduced by at least 25%, or by at least 33%, or by at least 50%.

Figure 7:
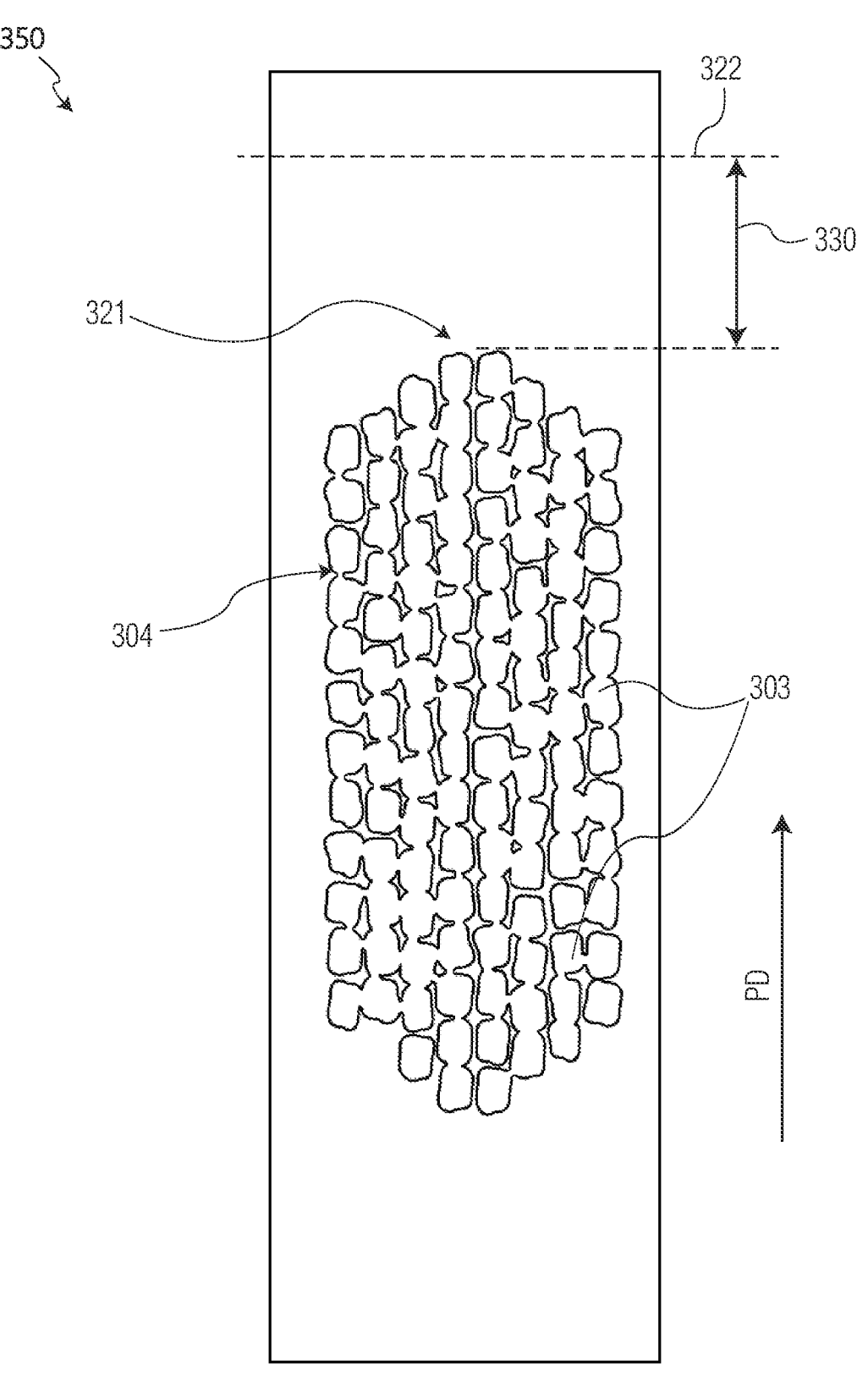
FIG. 7 is a schematic depiction of an exemplary modified filtered image based on the captured image of FIG. 5 and according to aspects of the present disclosure.

FIG. 7 is an exemplary depiction of a modified first captured image 350 after the described light transmittance (and optionally area filtering) technique as well as one or more dilation morphological operations have been performed. As can be seen, boundaries of the apertures 303 have been expanded, with the boundaries of a number of the apertures 303 merging to form fewer but larger, interconnected apertures 303. As mentioned, the image modification module 123 in some embodiments may perform multiple dilation morphological operations until a single interconnected aperture 303 is formed.

Once the image modification module 123 has modified the first captured image according to the above description, the registration module 125 can determine one or more features of the modified first captured image and, based on the one or more determined features, adjust the process 100 to ensure a proper registration of the apertured region(s) of the web material 112 is achieved relative to the chassis web 150. According to some embodiments, the registration module 125 may be configured to determine a first feature of interest related to the identified (and modified) apertured region or regions of the modified first captured image.

In some embodiments, the first feature of interest may be a leading edge of a leading identified/determined apertured region or regions of the modified first captured image—for example leading edge 321 of FIG. 7, which has also been superimposed as leading edge 322 on the exemplary first captured image 300 of FIG. 5. The leading region or regions may be that apertured region(s) disposed most close to the top of the modified first captured image—the top being the edge most leading in the process direction PD. More specifically, the registration module 125 may be configured to determine the leading edge by determining a transition in the modified first captured image, starting from a top edge of the image, where a pixel or pixels of the modified first captured image change from the second identification value to the first identification value. In other embodiments where the pixels are not assigned separate identification values, the registration module 125 may determine the leading edge where the registration module 125 determines a transition in the pixels from lower transmittance values to higher transmittance values. A transition from higher transmittance values to lower transmittance values would indicate a trailing edge of the identified apertured region or regions.

In further embodiments, rather than using a determined leading edge as the first feature of interest, the registration module 125 may determine a center of the apertured region or regions determined from the modified first captured image. Alternatively, a trailing edge may be used. In still other embodiments different features of the identified apertured region or regions in the modified first captured image may be used as a first feature of interest.

According to some embodiments, the registration module 125 may be further configured to determine a first reference feature of the modified first captured image, such as indicated by step 204. This first reference feature may be a top of the modified first captured image. Alternatively, the first reference feature may be a determined location, such as location 322 of FIG. 5, where the apertured web material 112 is expected to be cut by knife roll 164. Such determined locations may be automatically determined by a commercially available registration and/or inspection system, where used. Although, the reference location may be yet another feature of the modified first captured image.

The registration module 125 may further determine a first difference value by determining a difference in location of the first feature of interest and the first reference feature, indicated by distance 330. The registration module 125 may then compare the determined first difference value to a first difference value threshold or, alternatively, a first difference value threshold range. If the first difference value is above the first difference value threshold, or alternatively outside of the first difference value threshold range, the registration module 125 may take one or more actions to affect the registration of the apertured region(s) of the web material 112 relative to the chassis web 150, for example by adjusting the infeed speed of the web material 112, as indicated by step 208.

As one illustrative example, a first difference value threshold range may be between (and including) 5 mm and 15 mm. Accordingly, where the determined first difference value is anywhere between and including 5 mm and 15 mm, the registration module 125 may take no action. However, where the determined first difference value is less than 5 mm, the registration module 125 may be configured to slow down the infeed speed of the web material 112—for example by adjusting the rotational speed of feed rolls 116. Likewise, where the determined first difference value is greater than mm, the registration module 125 may be configured to speed up the infeed speed of the web material 112. Similarly, such a control operation may be applied where the first difference value threshold is a single value line, with the registration module 125 slowing down the infeed speed of the web material 112 where the determined first difference value is less than the first difference value threshold and speeding up the infeed speed of the web material 112 where the determined first difference value is greater than the first difference value threshold. However, it should be understood that the range of 5 mm and 15 mm represents just one exemplary embodiment and even further that a range in units of mm is not required. For example, the determined first difference value could represent a number of pixels along an axis of the modified first captured image.

Additionally, although the various functions—e.g. the filtering, dilation, identification, and determining functions—were described with respect to specific steps 202, 204, 206 and with respect to particular modules 123, 125, it should be understood that the present disclosure is not intended to be limited by such a strict description. For example, the determining of the apertured area(s) may be a separate step from the determining the apertured area first feature interest and the first reference feature. Additionally, in some embodiments, it may be the image modification module 123 which determines the apertured area and, optionally, the apertured area first feature of interest and the first reference feature. Accordingly, it should be understood that the particular sequence and breakdown of the process 200, and which modules 123, 125, or other modules, perform such steps and step portions detailed in FIG. 3 is not critical to effect the registration of the apertured web material 112 with respect to the chassis web 150.

According to further embodiments of the present disclosure, registration process 250 provides a further, more robust registration process by accounting for where the identified apertured region or regions are located after application to chassis web 150. For example, process 250 includes steps 252, 254, 256, and 258, which are equivalent to steps 202, 204, 206, and 208 of process 200. The registration process 250 further includes step 260 of combining the apertured web material 112 with the chassis web 150, for example by use of web combiner 155.

After combining the apertured web material 112 with the chassis web 150, the process 250 further comprises capturing a second image comprising the combined web 170 including both the apertured web material 112 and the chassis web 150, as indicated at step 262. According to some embodiments, the image capture module 121 may trigger the second image capture device 132 to capture a second image comprising the combined web 170 and store the second captured image in the storage device(s) 124.

Figure 8:
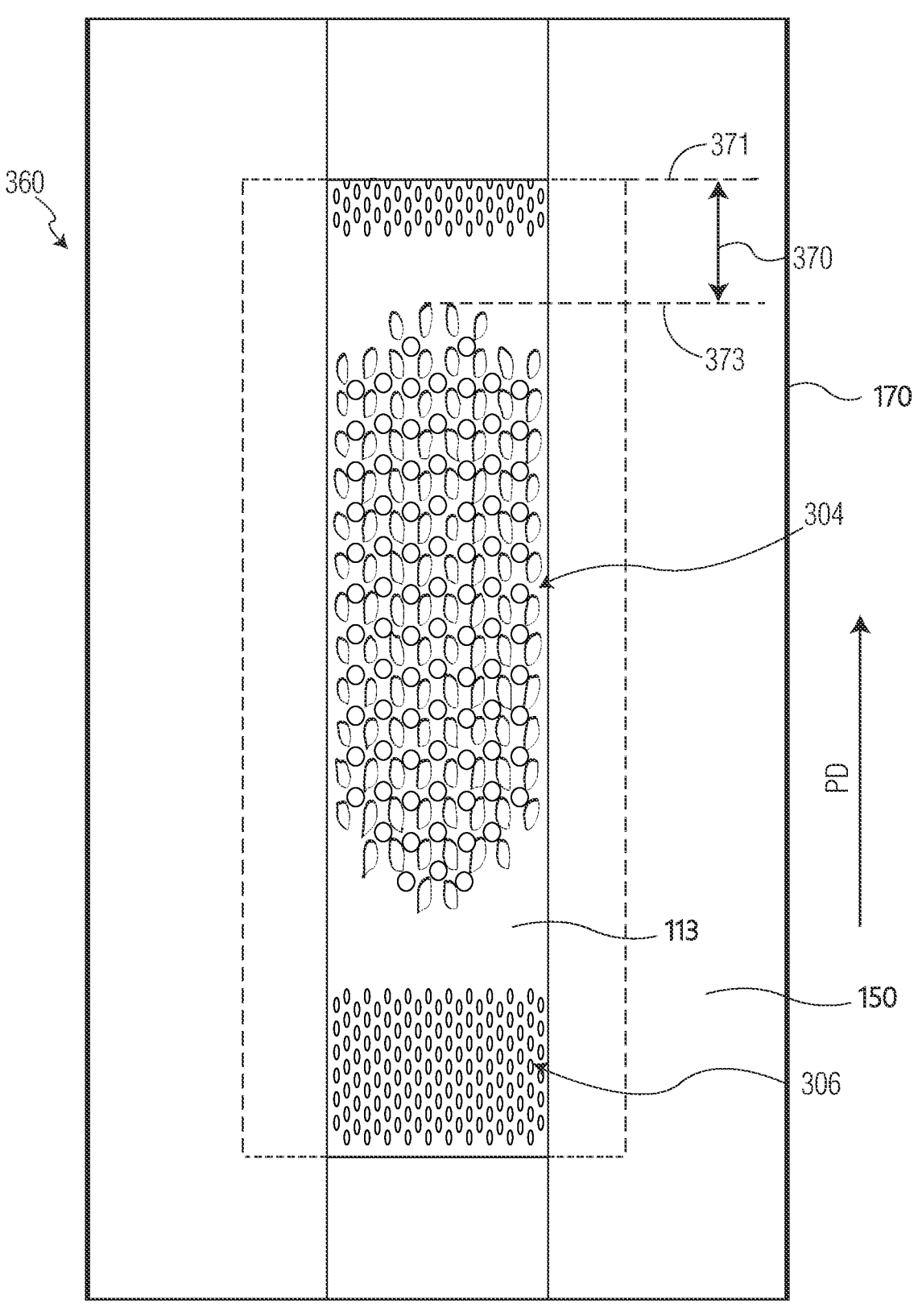
FIG. 8 is a schematic depiction of an exemplary image of a combined web which may be captured by the manufacturing process of FIG. 2.

FIG. 8 is a schematic depiction of an exemplary second captured image 360 detailing a discrete piece 113 of the apertured web material 112 coupled to chassis web 150. As can be seen, the portion 301 of the depicted apertured material has a length in the longitudinal direction, which corresponds to the process direction PD, which is less than a longitudinal length of the portion of the combined web 170. The second captured image 360 further details a leading edge 373 of the apertured region 304 as well as a leading edge 371 of the portion 301, with a distance between the edges 373, 371 shown as distance 370.

Using the second captured stored image, the image modification module 123 may next determine, or identify, one or more apertured regions, as indicated at step 264. In some embodiments, the image modification module 123 may perform any of the filtering functions described with respect to image modification module 123 at step 254 of process 250 (and step 204 of process 200) in order to identify or determine one or more apertured regions. In at least some of these embodiments, the image modification module 123 may be configured to filter the second captured image of step 262 in a manner differently than in the step 254. For example, the image modification module 123 may use a different light transmittance threshold (lower or higher) for step 264 than for step 254 and/or a different area threshold (lower or higher) in step 264 than for step 254.

The image modification module 123 may further perform a dilation morphological operation on the second captured (and filtered) image in some embodiments. The image modification module 123 may even perform multiple dilation morphological operations. As with step 254 and (step 204 of process 200), according to some embodiments, the image modification module 123 may perform such a dilation operation until there is only a single, unified aperture (e.g. region of pixels) having the first identification value (or light transmittance values equal to or greater than the threshold transmittance value). Although, in other embodiments, the image modification module 123 may perform such a dilation operation until the number of identified discrete, individual apertures having the first identification value (or light transmittance values equal to or greater than the threshold transmittance value) is reduced by at least 25%, or by at least 33%, or by at least 50%.

Once the image modification module 123 has modified the second captured image as described above, the registration module 125 can determine one or more features of interest of the modified second captured image (termed second feature(s) of interest herein) and, based on the one or more determined second features of interest, adjust the process 100 to ensure a proper registration of the apertured region(s) of the web material 112 is achieved relative to the chassis web 150. As with step 204 of process 200, step 264 may include the registration module 125 determining a second feature of interest related to the identified or determined apertured region or regions of the second modified captured image.

Similar to the description of process 200 and the first feature of interest, in some embodiments, the second feature of interest at step 264 may be a leading edge of a leading apertured region or regions of the modified second captured image—for example as indicated by leading edge 373 of FIG. 8. The registration module 125 may be configured to determine the leading edge by any manner described above with respect to step 204 of process 200. In further embodiments, however, the registration module 125 may determine a center of the apertured region or regions determined from the modified second captured image rather than a leading edge. Alternatively, a trailing edge may be used. In still other embodiments different features of the identified apertured region or regions in the modified second captured image may be used as a second feature of interest.

According to some embodiments, the registration module 125 may be further configured to determine a reference feature of the modified second captured image (termed a second reference feature herein), such as indicated by step 266. This second reference feature may be an edge of the discrete piece of apertured material 113, such as a leading edge—for example, leading edge 371 of FIG. 8. Such material edge detection may be accomplished through identification in transitions of transmittance levels, as is well-known in the art. Alternatively, the second reference feature may be an edge of the second captured image 360 (top or bottom), or even the trailing edge of the portion 301 of apertured material. It should be understood that the specific second reference feature is not critical and that any suitable second reference feature may be used.

The registration module 125 may further determine a second difference value by determining a difference in location of the second feature of interest and the second reference feature with respect to the second modified captured image, for example as indicated by distance 370. The registration module 125 may then compare the second determined difference value to a second difference value threshold or, alternatively, a second difference value threshold range. If the second difference value is above the second difference value threshold, or alternatively outside of the second difference value threshold range, the registration module 125 may take one or more actions to change the registration of the apertured region(s) of the web material 112 relative to the chassis web 150.

In such situations where the second difference value is above the second difference value threshold, or alternatively outside of the second difference value threshold range, the registration module 125 may be configured to adjust a registration parameter used by the system 110 to effect the registration of the apertured web material 112 with respect to the chassis web 150. For example, the registration module 125 may be configured to add an offset to the difference determination of step 258. As one illustrative example, where the second difference value is above the second difference value threshold by 5 mm, the registration module 125 may be configured to add an offset value of +5 mm to the first determined difference value of step 258. Accordingly, where the first determined difference value of step 258 is compared to the first difference value threshold, adding the +5 mm offset value will cause the first determined difference value to be larger than if the first determined difference value were determined just based on information from the modified first captured image. If the +5 mm offset value causes the first determined difference value at step 258 to be greater than the first difference value threshold, then registration module 125 may take one or more actions to affect the registration of the apertured region(s) of the web material 112 relative to the chassis web 150 as described previously. Likewise, if the second determined difference value is smaller than the second determined difference value threshold, the registration module 125 may add a negative offset value to the first determined difference value of step 258. In this manner, the process 250 may account for registration errors occurring after the cutting of the apertured web material 112 by knife roll 164, such as with the web combiner 155.

Where the second determined difference value of step 258 is compared to a second difference value threshold range, adding or subtracting an offset value may not be enough to push the first determined difference value outside of the first difference value threshold range and thereby cause a change in the registration of the apertured web material 112 with respect to the chassis web 150. Accordingly, in some of further embodiments, rather than use add or subtract an offset value with respect to the first determined difference value of step 258, the registration module 125 may be configured to directly adjust the infeed speed of the web material 112 to achieve proper registration of the apertured web material 112 with respect to the chassis web 150. In at least some of these embodiments, the registration module 125 may further be configured to add an offset value to the first difference value threshold range.

As one illustrative example, the first difference value threshold range may be between (and including) 5 mm and 15 mm, the first determined difference value may be 10 mm, and the second determined difference value is of the second difference value threshold range (or above a second difference value threshold) by 5 mm. By only directly adjusting the infeed speed of the web material 112, in a stable system, the first determined difference value would become 15 mm. Accordingly, while the second determined difference value may be within the appropriate second difference value threshold range (or at the appropriate second difference value threshold), a small deviation of the first determined difference value may throw the first determined difference value outside of the first difference value threshold range (or above the first difference value threshold). For this reason, in such embodiments, the registration module 125 may further adjust the first difference value threshold range by adding 5 mm to the low and high ends of the range, such that the first difference value threshold range would be adjusted to be between (and including) 10 mm and 20 mm. In this manner, further small changes in the first determined difference value may not be enough to cause a change in the registration of the apertured web material 112 with respect to the chassis web 150.

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

EMBODIMENTS

Embodiment 1: A method of registering first and second simultaneously advancing webs may comprise moving a continuous first web in a machine direction, moving a continuous second web in the machine direction in proximity to the first web, the second web comprising one or more first portions having a light transmittance value below a transmittance threshold value and one or more second portions having a light transmittance value greater than or equal to the transmittance threshold value, capturing, with a registration system comprising an image capture device coupled to a registration processing device, a first image comprising a portion of the second web, filtering, with the registration processing device, the captured first image to determine one or more regions of the captured first image having a light transmittance value greater than the transmittance threshold value, modifying, with the registration processing device, the captured first image by applying a dilation morphological operation to the filtered captured first image, determining, with the registration processing device and based at least in part on the modified captured first image, a feature of interest related to the determined one or more regions, determining, with the registration processing device, a first difference value comprising a difference in location between the feature of interest and a reference feature of the captured first image or the modified captured first image, adjusting, based at least in part on the determined first difference value, a speed of the second web in the machine direction, and coupling the first web and the second web together.

Embodiment 2: The method of embodiment 1, wherein the feature of interest related to the determined one or more regions may comprise a leading edge, in the machine direction, of the determined one or more regions.

Embodiment 3: The method of any one of embodiment 1 or 2, wherein if the determined first difference value is above a first difference value threshold, the speed of the second web may be increased in the machine direction.

Embodiment 4: The method of any one of embodiments 1-3, wherein if the determined first difference value is below a first difference value threshold, the speed of the second web may be decreased in the machine direction.

Embodiment 5: The method of embodiment 3, wherein the first difference value threshold is a maximum value of a first difference value threshold range.

Embodiment 6: The method of any one of embodiments 1-5, wherein the registration processing device may apply the dilation morphological operation multiple times to the filtered captured first image.

Embodiment 7: The method of embodiment 6, wherein the registration processing device may apply the dilation morphological operation such that a total number of discrete determined regions having a light transmittance value greater than the transmittance threshold value is reduced by at least 25%.

Embodiment 8: The method of embodiment 6, wherein the registration processing device may apply the dilation morphological operation to result in a single, unified region having a light transmittance value greater than the transmittance threshold value.

Embodiment 9: The method of any one of embodiments 1-8, further comprising filtering, with the registration processing device, the captured first image to determine one or more regions of the captured first image that have both a light transmittance value greater than the transmittance threshold value and have an area larger than a threshold area.

Embodiment 10: A method of registering a first web and an apertured region of a second web may comprise moving a continuous first web in a machine direction, moving a continuous second web in the machine direction in proximity to the first web, the second web comprising a plurality of apertures forming a plurality of discrete apertured regions spaced apart from each other in the machine direction, capturing, with a registration system comprising an image capture device coupled to a registration processing device, a first image comprising a portion of the second web, filtering, with the registration processing device, the captured first image to determine one or more apertured regions of the captured first image, modifying, with the registration processing device, the filtered captured first image by applying a dilation morphological operation to the filtered captured first image, determining, with the registration processing device and based at least in part on the modified filtered captured first image, a feature of interest related to the determined one or more apertured regions, determining, with the registration processing device, a first difference value comprising a difference in location between the feature of interest and a reference feature of the captured first image or the modified filtered captured first image, adjusting, based at least in part on the determined first difference value, a relative position of a discrete apertured region of first web with respect to the second web, and combining the first web and the second web.

Embodiment 11: The method of embodiment 10, wherein filtering, with the registration processing device, the captured first image to determine one or more apertured regions of the captured first image may comprise filtering the captured first image to determine one or more regions of the captured first image having a light transmittance value greater than the transmittance threshold value.

Embodiment 12: The method of any one of embodiment 10 or 11, wherein adjusting, based at least in part on the determined first difference value, a relative position of a discrete apertured region of first web with respect to the second web may comprise speeding up or slowing down one of the first web and the second web.

Embodiment 13: The method of any one of embodiments 10-12, wherein combining the first web and the second web may comprise cutting the first web into discrete first web portions and applying the discrete first web portions to the second web in a spaced apart fashion.

Embodiment 14: The method of claim 10 wherein adjusting, based at least in part on the determined first difference value, a relative position of a discrete apertured region of first web with respect to the second web may comprise advancing the relative position of a discrete apertured region of first web in the machine direction with respect to the second web if the determined first difference value is greater than a first threshold difference value and retreating the relative position of a discrete apertured region of first web in the machine with respect to the second web if the determined first difference value is less than a second threshold difference value.

Embodiment 15: A method of registering a first web and an apertured region of a second web may comprise moving a continuous first web in a machine direction, moving a continuous second web in the machine direction in proximity to the first web, the second web comprising a plurality of apertures forming a plurality of discrete apertured regions spaced apart from each other in the machine direction, capturing, with a registration system comprising a first image capture device coupled to a registration processing device, a first image comprising a portion of the second web, determining, with the registration processing device, a first difference value comprising a difference in location between a first feature of interest and a first reference feature of the captured first image, adjusting, based at least in part on registration parameters including the determined first difference value and a first difference value threshold, a relative position of a discrete apertured region of the second web with respect to the first web, combining the first web and the second web, capturing, with the registration system by a second image capture device coupled to the registration processing device, a second image comprising a portion of the combined first web and second web, determining, with the registration processing device, a second difference value comprising a difference in location between a second feature of interest and a second reference feature of the captured second image, and adjusting, with the registration processing device and based at least on the determined second difference value, at least one of the registration parameters.

Embodiment 16: The method of embodiment 15, wherein the registration parameters may include the determined first difference value and a first difference value threshold range instead of a first difference value threshold.

Embodiment 17: The method of any one of embodiment 15 or 16, further comprising: filtering, with the registration processing device, the captured first image to determine one or more apertured regions of the captured first image, modifying, with the registration processing device, the filtered captured first image by applying a dilation morphological operation to the filtered captured first image, and determining, with the registration processing device and based at least in part on the modified filtered captured first image, the first feature of interest related to the determined one or more apertured regions of the modified filtered captured first image.

Embodiment 18: The method of embodiment 17, wherein the first feature of interest of the determined one or more regions may comprise a leading edge in the machine direction of the determined one or more regions.

Embodiment 19: The method of any one of embodiments 15-18, further comprising filtering, with the registration processing device, the captured second image to determine one or more apertured regions of the captured second image, modifying, with the registration processing device, the filtered captured second image by applying a dilation morphological operation to the filtered captured second image, and determining, with the registration processing device and based at least in part on the modified filtered captured second image, a second feature of interest related to the determined one or more apertured regions of the modified filtered captured second image.

Embodiment 20: The method of any one of embodiments 15-19, wherein adjusting, with the registration processing device and based at least on the determined second difference value, at least one of the registration parameters may comprise adding an offset value to the first difference value.

Embodiment 21: The method of any one of embodiments 15-20, wherein adjusting, with the registration processing device and based at least on the determined second difference value, at least one of the registration parameters may comprise adjusting the first difference value threshold.

Embodiment 22: A system for registering an apertured region of a first web with respect to a second web, the system comprising: a first image capture device; infeed rolls for feeding the first web in a process direction; and a registration processing device coupled to the first image capture device and the infeed rolls. The registration processing device may be configured to: capture, with first image capture device, a first image comprising a portion of the first web; filter the captured first image to determine one or more regions of the captured first image having a light transmittance value greater than the transmittance threshold value; modify the captured first image by applying a dilation morphological operation to the filtered captured first image; determine, based at least in part on the modified captured first image, a first feature of interest related to the determined one or more regions; determine a first difference value comprising a difference in location between the first feature of interest and a reference feature of the captured first image or the modified captured first image; adjust, based at least in part on registration parameters including the determined first difference value and a first difference value threshold, a speed of the first web by changing a rotational speed of the infeed rolls.

Embodiment 23: The system of embodiment 22, wherein the first feature of interest related to the determined one or more regions comprises a leading edge, in the machine direction, of the determined one or more regions.

Embodiment 24: The system of any one of embodiment 22 or 23, wherein if the determined first difference value is above the first difference value threshold, the speed of the first web is increased.

Embodiment 25: The system of any one of embodiments 22-24, wherein if the determined first difference value is below the first difference value threshold, the speed of the first web is decreased.

Embodiment 26: The system of any one of embodiments 22-24, wherein the first difference value threshold is a maximum value of a first difference value threshold range.

Embodiment 27: The system of any one of embodiments 22-26, wherein the registration processing device may apply the dilation morphological operation multiple times to the filtered captured first image.

Embodiment 28: The system of embodiment 27, wherein the registration processing device may apply the dilation morphological operation such that a total number of discrete determined regions having a light transmittance value greater than the transmittance threshold value is reduced by at least 25%.

Embodiment 29: The system of embodiment 27, wherein the registration processing device may apply the dilation morphological operation to result in a single, unified region having a light transmittance value greater than the transmittance threshold value.

Embodiment 30: The system of any one of embodiments 22-29, wherein the registration processing device may further be configured to filter the captured first image to determine one or more regions of the captured first image that have both a light transmittance value greater than the transmittance threshold value and have an area larger than a threshold area.

Embodiment 31: The system of any one of embodiments 22-30, further comprising a web combiner for combining the first web and the second web and a second image capture device, the second image capture device coupled to the registration processing device, and wherein the registration processing device is further configured to: capture, with the second image capture device, a second image comprising a portion of the combined first web and second web; determine a second difference value comprising a difference in location between a second feature of interest and a second reference feature of the captured second image; and adjust, based at least on the determined second difference value, at least one of the registration parameters.

Embodiment 32: The system of embodiment 31, wherein the registration parameters include the determined first difference value and a first difference value threshold range instead of a first difference value threshold.

Embodiment 33: The system any one of embodiment 31 or 32, wherein the registration processing device is further configured to filter the captured second image to determine one or more apertured regions of the captured second image; modify the filtered captured second image by applying a dilation morphological operation to the filtered captured second image; and determine, based at least in part on the modified filtered captured second image, a second feature of interest related to the determined one or more apertured regions of the modified filtered captured second image.

Embodiment 34: The system of any one of embodiments 31-33, wherein adjusting, based at least on the determined second difference value, at least one of the registration parameters may comprise adding an offset value to the first difference value.

Embodiment 35: The system of any one of embodiments 31-33, wherein adjusting, with the registration processing device and based at least on the determined second difference value, at least one of the registration parameters may comprise adjusting the first difference value threshold.

What is claimed is:

1. A method of registering first and second simultaneously advancing webs, the method comprising:

moving a continuous first web in a machine direction;

moving a continuous second web in the machine direction in proximity to the first web, the second web comprising one or more first portions having a light transmittance value below a transmittance threshold value and one or more second portions having a light transmittance value greater than or equal to the transmittance threshold value;

capturing, with a registration system comprising an image capture device coupled to a registration processing device, a first image comprising a portion of the second web;

filtering, with the registration processing device, the captured first image to determine one or more regions of the captured first image having a light transmittance value greater than the transmittance threshold value;

modifying, with the registration processing device, the captured first image by applying a dilation morphological operation to the filtered captured first image;

determining, with the registration processing device and based at least in part on the modified captured first image, a feature of interest related to the determined one or more regions;

determining, with the registration processing device, a first difference value comprising a difference in location between the feature of interest and a reference feature of the captured first image or the modified captured first image;

adjusting, based at least in part on the determined first difference value, a speed of the second web in the machine direction; and coupling the first web and the second web together, wherein the registration processing device applies the dilation morphological operation multiple times to the filtered captured first image, and wherein the registration processing device applies the dilation morphological operation such that a total number of discrete determined regions having a light transmittance value greater than the transmittance threshold value is reduced by at least 25%.

2. The method of claim 1, wherein the feature of interest related to the determined one or more regions comprises a leading edge, in the machine direction, of the determined one or more regions.

3. The method of claim 1, wherein if the determined first difference value is above a first difference value threshold, the speed of the second web is increased in the machine direction.

4. The method of claim 1, wherein if the determined first difference value is below a first difference value threshold, the speed of the second web is decreased in the machine direction.

5. The method of claim 3, wherein the first difference value threshold is a maximum value of a first difference value threshold range.

6. The method of claim 1, wherein the registration processing device applies the dilation morphological operation to result in a single, unified region having a light transmittance value greater than the transmittance threshold value.

7. The method of claim 1, further comprising filtering, with the registration processing device, the captured first image to determine one or more regions of the captured first image that have both a light transmittance value greater than the transmittance threshold value and have an area larger than a threshold area.

8. A method of registering a first web and an apertured region of a second web, the method comprising:

moving a continuous first web in a machine direction;

moving a continuous second web in the machine direction in proximity to the first web, the second web comprising a plurality of apertures forming a plurality of discrete apertured regions spaced apart from each other in the machine direction;

capturing, with a registration system comprising an image capture device coupled to a registration processing device, a first image comprising a portion of the second web;

filtering, with the registration processing device, the captured first image to determine one or more apertured regions of the captured first image;

modifying, with the registration processing device, the filtered captured first image by applying a dilation morphological operation to the filtered captured first image;

determining, with the registration processing device and based at least in part on the modified filtered captured first image, a feature of interest related to the determined one or more apertured regions;

determining, with the registration processing device, a first difference value comprising a difference in location between the feature of interest and a reference feature of the captured first image or the modified filtered captured first image;

adjusting, based at least in part on the determined first difference value, a relative position of a discrete apertured region of first web with respect to the second web; and combining the first web and the second web, wherein the image capture device comprises an optical system including an image sensor.

9. The method of claim 8, wherein filtering, with the registration processing device, the captured first image to determine one or more apertured regions of the captured first image comprises filtering the captured first image to determine one or more regions of the captured first image having a light transmittance value greater than the transmittance threshold value.

10. The method of claim 8, wherein adjusting, based at least in part on the determined first difference value, a relative position of a discrete apertured region of first web with respect to the second web comprises speeding up or slowing down one of the first web and the second web.

11. The method of claim 8, wherein combining the first web and the second web comprises cutting the first web into discrete first web portions and applying the discrete first web portions to the second web in a spaced apart fashion.

12. The method of claim 8 wherein adjusting, based at least in part on the determined first difference value, a relative position of a discrete apertured region of first web with respect to the second web comprises advancing the relative position of a discrete apertured region of first web in the machine direction with respect to the second web if the determined first difference value is greater than a first threshold difference value and retreating the relative position of a discrete apertured region of first web in the machine with respect to the second web if the determined first difference value is less than a second threshold difference value.

13. A method of registering a first web and an apertured region of a second web, the method comprising:

moving a continuous first web in a machine direction;

moving a continuous second web in the machine direction in proximity to the first web, the second web comprising a plurality of apertures forming a plurality of discrete apertured regions spaced apart from each other in the machine direction;

capturing, with a registration system comprising a first image capture device coupled to a registration processing device, a first image comprising a portion of the second web;

determining, with the registration processing device, a first difference value comprising a difference in location between a first feature of interest and a first reference feature of the captured first image;

adjusting, based at least in part on registration parameters including the determined first difference value and a first difference value threshold, a relative position of a discrete apertured region of the second web with respect to the first web;

combining the first web and the second web;

capturing, with the registration system by a second image capture device coupled to the registration processing device, a second image comprising a portion of the combined first web and second web;

determining, with the registration processing device, a second difference value comprising a difference in location between a second feature of interest and a second reference feature of the captured second image; and adjusting, with the registration processing device and based at least on the determined second difference value, at least one of the registration parameters, wherein each of the first image capture device and the second image capture device comprises an optical system including an image sensor.

14. The method of claim 13, wherein the registration parameters include the determined first difference value and a first difference value threshold range instead of a first difference value threshold.

15. The method of claim 13, further comprising:

filtering, with the registration processing device, the captured first image to determine one or more apertured regions of the captured first image;

modifying, with the registration processing device, the filtered captured first image by applying a dilation morphological operation to the filtered captured first image; and determining, with the registration processing device and based at least in part on the modified filtered captured first image, the first feature of interest related to the determined one or more apertured regions of the modified filtered captured first image.

16. The method of claim 15, wherein the first feature of interest of the determined one or more regions comprises a leading edge in the machine direction of the determined one or more regions.

17. The method of claim 13, further comprising:

filtering, with the registration processing device, the captured second image to determine one or more apertured regions of the captured second image;

modifying, with the registration processing device, the filtered captured second image by applying a dilation morphological operation to the filtered captured second image; and determining, with the registration processing device and based at least in part on the modified filtered captured second image, a second feature of interest related to the determined one or more apertured regions of the modified filtered captured second image.

18. The method of claim 13, wherein adjusting, with the registration processing device and based at least on the determined second difference value, at least one of the registration parameters comprises adding an offset value to the first difference value.

19. The method of claim 13, wherein adjusting, with the registration processing device and based at least on the determined second difference value, at least one of the registration parameters comprises adjusting the first difference value threshold.

* * * * *